United States Patent
Mikami et al.

(10) Patent No.: US 10,517,467 B2
(45) Date of Patent: Dec. 31, 2019

(54) FOCUS CONTROL DEVICE, ENDOSCOPE APPARATUS, AND METHOD FOR CONTROLLING FOCUS CONTROL DEVICE

(71) Applicant: OLYMPUS CORPORATION, Hachioji-shi, Tokyo (JP)

(72) Inventors: Toshiaki Mikami, Hachioji (JP); Manabu Ichikawa, Hachioji (JP); Koichiro Yoshino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 63 days.

(21) Appl. No.: 15/613,092

(22) Filed: Jun. 2, 2017

(65) Prior Publication Data
US 2017/0265726 A1 Sep. 21, 2017

Related U.S. Application Data

(63) Continuation of application No. PCT/JP2014/081805, filed on Dec. 2, 2014.

(51) Int. Cl.
| | |
|---|---|
| *A61B 1/00* | (2006.01) |
| *A61B 1/045* | (2006.01) |
| *A61B 1/313* | (2006.01) |
| *H04N 5/225* | (2006.01) |
| *H04N 5/232* | (2006.01) |

(Continued)

(52) U.S. Cl.
CPC ...... *A61B 1/00188* (2013.01); *A61B 1/00006* (2013.01); *A61B 1/00009* (2013.01);
(Continued)

(58) Field of Classification Search
CPC ............ A61B 1/00188; A61B 1/00006; A61B 1/0009; A61B 1/045; A61B 1/3132;
(Continued)

(56) References Cited

U.S. PATENT DOCUMENTS

| 5,416,515 A | 5/1995 | Arai et al. |
| 8,994,874 B2 * | 3/2015 | Iwasaki ............. H04N 5/23212 |
| | | 348/349 |

(Continued)

FOREIGN PATENT DOCUMENTS

| JP | 63017417 A | 1/1988 |
| JP | 64077008 A | 3/1989 |

(Continued)

OTHER PUBLICATIONS

International Search Report (ISR) and Written Opinion dated Mar. 3, 2015 issued in International Application No. PCT/JP2014/081805.

*Primary Examiner* — Twyler L Haskins
*Assistant Examiner* — Fayez Bhuiyan
(74) *Attorney, Agent, or Firm* — Holtz, Holtz & Volek PC

(57) ABSTRACT

A focus control device includes a processor including hardware, the processor being configured to implement: an area setting process that sets a plurality of areas to a captured image that has been captured by an imaging section, each of the plurality of areas including a plurality of pixels; a direction determination process that determines whether a target in-focus position lies in a NEAR direction or a FAR direction with respect to a reference position with respect to some or all of the plurality of areas set to the captured image to calculate a direction determination result with respect to each of the plurality of areas, the target in-focus position being a target of an in-focus object plane position; and a focus control process that preferentially brings an area among the plurality of areas that is situated away from the imaging section into focus based on the direction determination result.

18 Claims, 17 Drawing Sheets

(51) Int. Cl.
*G02B 7/34* (2006.01)
*G02B 7/38* (2006.01)
*G02B 23/24* (2006.01)
*G02B 23/26* (2006.01)

(52) U.S. Cl.
CPC ............ *A61B 1/045* (2013.01); *A61B 1/3132* (2013.01); *G02B 7/34* (2013.01); *H04N 5/2256* (2013.01); *H04N 5/23212* (2013.01); *H04N 5/23245* (2013.01); *G02B 7/38* (2013.01); *G02B 23/2469* (2013.01); *G02B 23/26* (2013.01); *H04N 2005/2255* (2013.01)

(58) Field of Classification Search
CPC ........ G02B 7/34; G02B 7/38; G02B 23/2469; H04N 5/2256; H04N 5/23212; H04N 5/23245
See application file for complete search history.

(56) References Cited

U.S. PATENT DOCUMENTS

| 2011/0305446 | A1* | 12/2011 | Itoh | G03B 13/36 396/95 |
| 2013/0188029 | A1* | 7/2013 | Takahashi | H04N 5/23212 348/65 |
| 2014/0300799 | A1* | 10/2014 | Yoshino | H04N 5/23212 348/347 |

FOREIGN PATENT DOCUMENTS

| JP | 06189187 A | 7/1994 |
| JP | 2006110055 A | 4/2006 |
| JP | 2006245792 A | 9/2006 |
| JP | 2008083456 A | 4/2008 |
| JP | 2014204337 A | 10/2014 |

* cited by examiner

FIG. 4

| G | R | G | R | G | R | G | R |
|---|---|---|---|---|---|---|---|
| B | G | B | G | B | G | B | G |
| G | R | G | R | G | R | G | R |
| B | G | B | G | B | G | B | G |
| G | R | G | R | G | R | G | R |
| B | G | B | G | B | G | B | G |
| G | R | G | R | G | R | G | R |
| B | G | B | G | B | G | B | G |

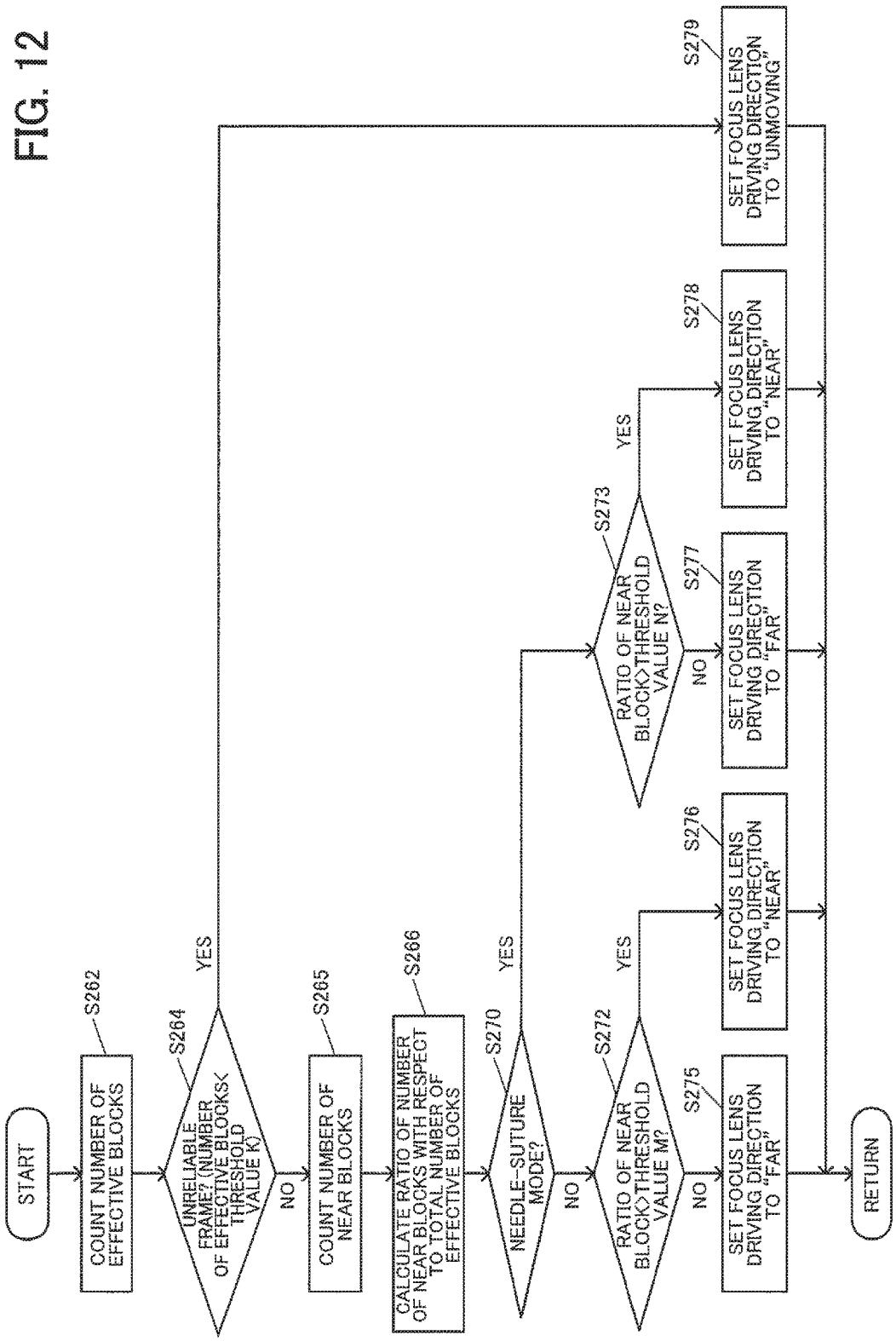

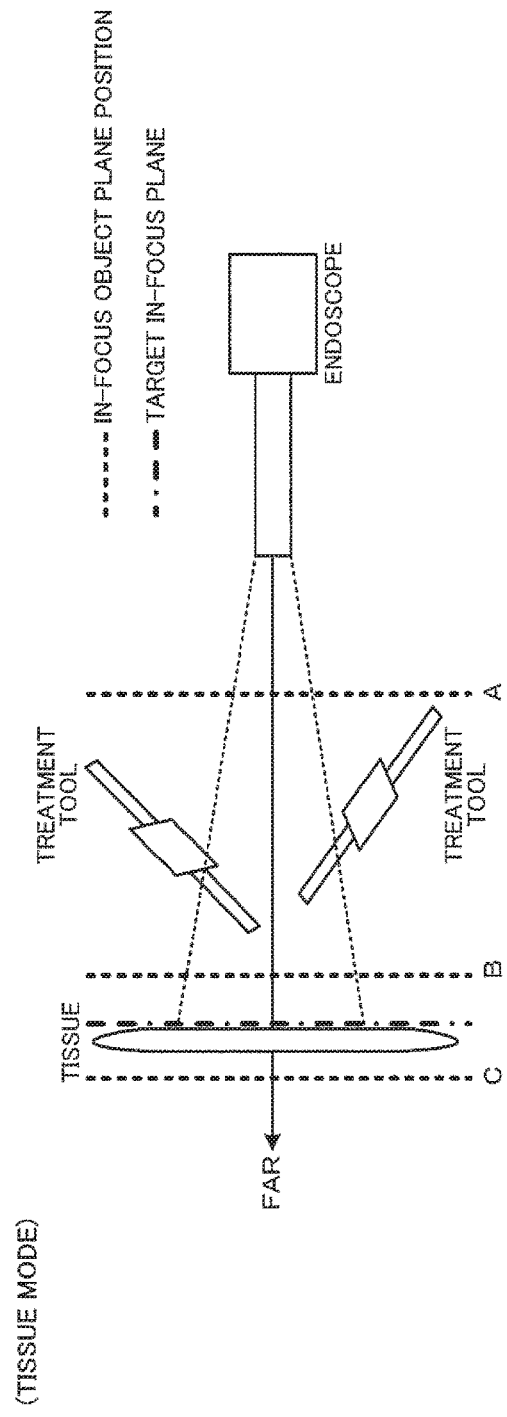

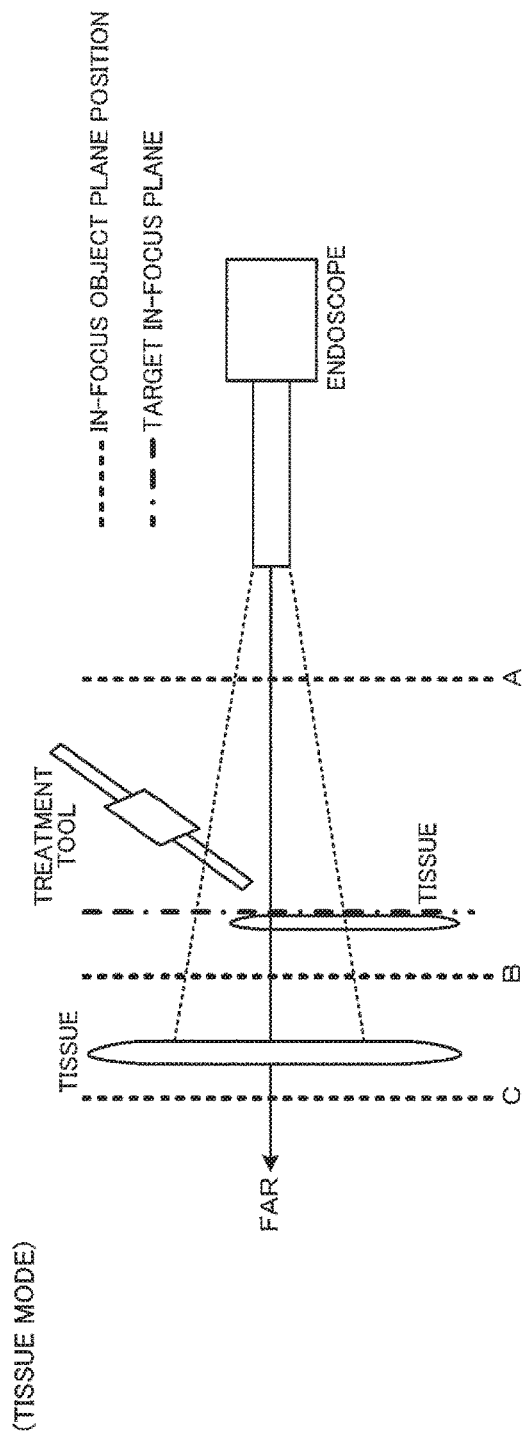

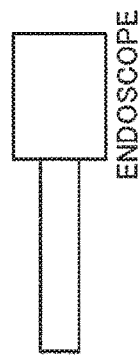
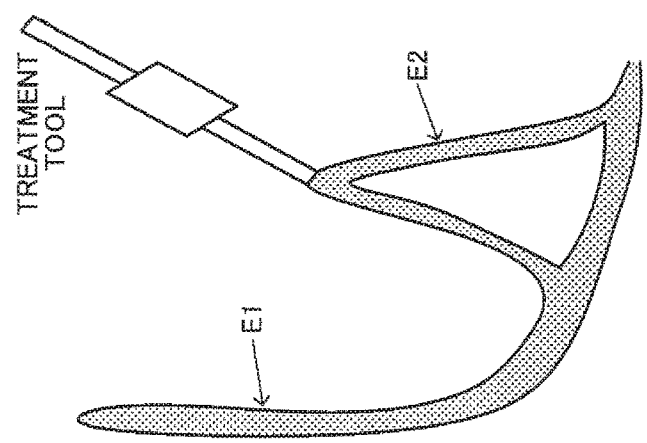
FIG. 15B
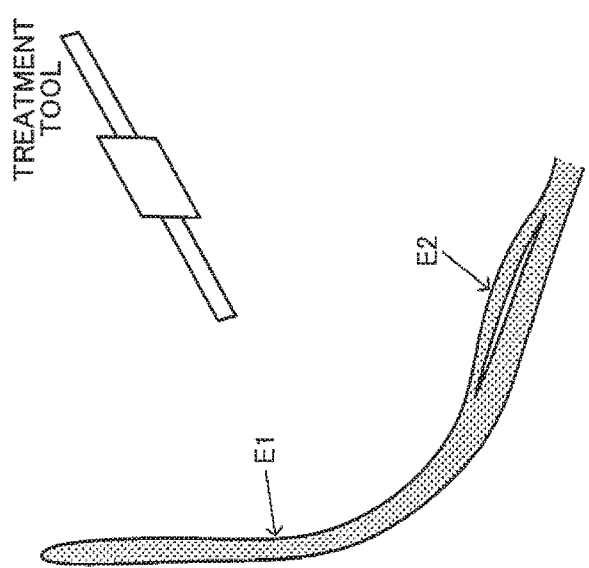
FIG. 15A (TISSUE MODE)

(NEEDLE-SUTURE MODE)

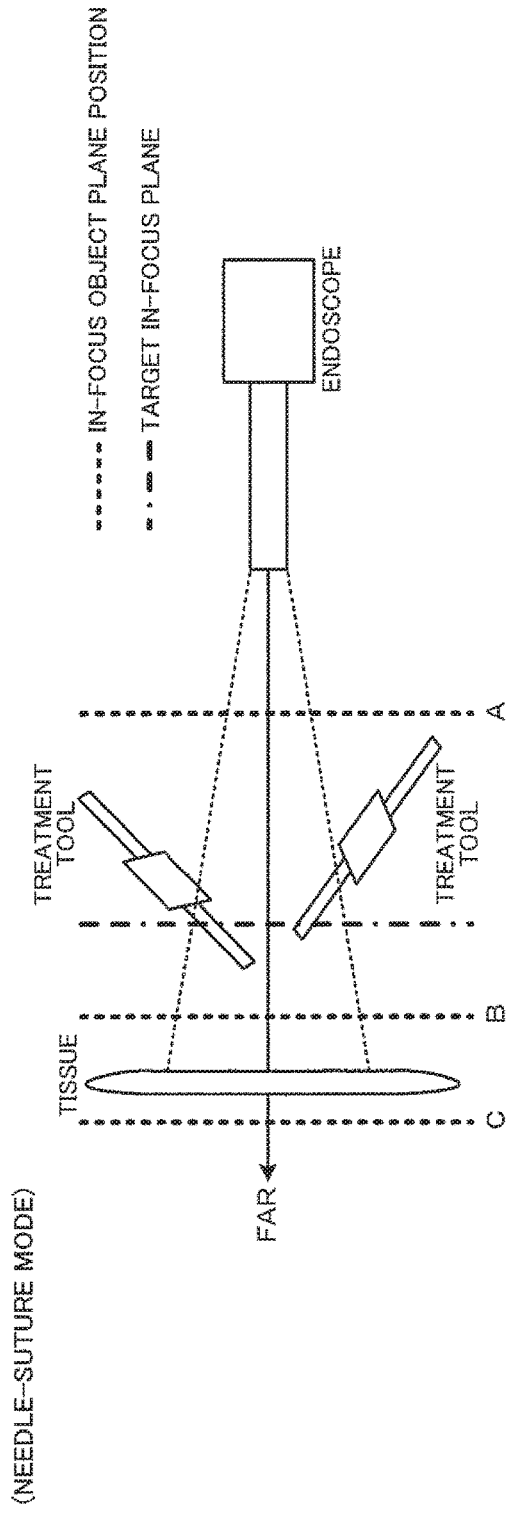

FOCUS CONTROL DEVICE, ENDOSCOPE APPARATUS, AND METHOD FOR CONTROLLING FOCUS CONTROL DEVICE

CROSS REFERENCE TO RELATED APPLICATION

This application is a continuation of International Patent Application No. PCT/JP2014/081805, having an international filing date of Dec. 2, 2014, which designated the United States.

BACKGROUND

The present invention relates to a focus control device, an endoscope apparatus, a method for controlling a focus control device, and the like.

A depth of field as deep as possible is required for an endoscope system so that the user can easily perform diagnosis and treatment. In recent years, the depth of field of an endoscope system has become shallow along with the use of an image sensor having a large number of pixels, and an endoscope system that performs an autofocus (AF) process has been proposed.

A treatment (e.g., lesion excision and suture) may be performed during an endoscopic procedure, and a treatment tool (e.g., electrosurgical knife and forceps) may lie between tissue (that is brought into focus) and an endoscope system (imaging device). In such a case, the treatment tool that has a contrast higher than that of tissue may be brought into focus instead of tissue.

JP-A-2006-245792 discloses a method that prompts the user to designate an obstacle that lies between the object of interest and the imaging device so that the object of interest is brought into focus.

SUMMARY

According to one aspect of the invention, there is provided a focus control device comprising:
 a processor comprising hardware,
 the processor being configured to implement:
 an area setting process that sets a plurality of areas to a captured image that has been captured by an imaging section, each of the plurality of areas including a plurality of pixels;
 a direction determination process that determines whether a target in-focus position lies in a NEAR direction or a FAR direction with respect to a reference position with respect to some or all of the plurality of areas set to the captured image to calculate a direction determination result with respect to each of the plurality of areas, the target in-focus position being a target of an in-focus object plane position; and
 a focus control process that preferentially brings an area among the plurality of areas that is situated away from the imaging section into focus based on the direction determination result,
 wherein the processor calculates at least one of area information about an area for which it has been determined that the target in-focus position lies in the NEAR direction, and the area information about an area for which it has been determined that the target in-focus position lies in the FAR direction, based on the direction determination result, and determines whether to perform the focus control process that moves the in-focus object plane position in the NEAR direction, or the focus control process that moves the in-focus object plane position in the FAR direction, based on whether or not the area information satisfies a given condition.

According to another aspect of the invention, there is provided a focus control device comprising:
 a processor comprising hardware,
 the processor being configured to implement:
 an area setting process that sets a plurality of areas to a captured image that has been captured by an imaging section, each of the plurality of areas including a plurality of pixels;
 a direction determination process that determines whether a target in-focus position lies in a NEAR direction or a FAR direction with respect to a reference position with respect to some or all of the plurality of areas set to the captured image to calculate a direction determination result with respect to each of the plurality of areas, the target in-focus position being a target of an in-focus object plane position; and
 a focus control process that preferentially brings an area among the plurality of areas that is situated away from the imaging section into focus based on the direction determination result,
 wherein the processor calculates an AF evaluation value with respect to each of the plurality of areas from a plurality of the captured images that include a first captured image and a second captured image, and implements the direction determination process based on a comparison process performed on the AF evaluation value calculated from the first captured image and the AF evaluation value calculated from the second captured image, the first captured image being an image captured in a state in which the in-focus object plane position lies in the NEAR direction with respect to the reference position, and the second captured image being an image captured in a state in which the in-focus object plane position lies in the FAR direction with respect to the reference position.

According to another aspect of the invention, there is provided a focus control device comprising:
 a processor comprising hardware,
 the processor being configured to implement:
 an image acquisition process that acquires a captured image that has been captured by an imaging section; and
 a focus control process that utilizes wobbling,
 wherein, when an in-focus object plane position that corresponds to a wobbling reference position lies between tissue and a treatment tool that is used to perform treatment on the tissue, the processor implements the focus control process that utilizes the wobbling that preferentially moves the in-focus object plane position in a first direction as compared with a second direction, the first direction being a direction toward the tissue with respect to the in-focus object plane position that corresponds to the wobbling reference position, and the second direction being a direction toward the treatment tool with respect to the in-focus object plane position that corresponds to the wobbling reference position.

According to another aspect of the invention, there is provided an endoscope apparatus comprising one of the above focus control device.

According to another aspect of the invention, there is provided a method for controlling a focus control device comprising:
 setting a plurality of areas to a captured image that has been captured by an imaging section, each of the plurality of areas including a plurality of pixels;
 performing a direction determination process that determines whether a target in-focus position lies in a NEAR direction or a FAR direction with respect to a reference position with respect to some or all of the plurality of areas set to the captured image to calculate a direction determination result with respect to each of the plurality of areas, the target in-focus position being a target of an in-focus object plane position;

performing a focus control process that preferentially brings an area among the plurality of areas that is situated away from the imaging section into focus based on the direction determination result; and calculating at least one of area information about an area for which it has been determined that the target in-focus position lies in the NEAR direction, and the area information about an area for which it has been determined that the target in-focus position lies in the FAR direction, based on the direction determination result, and determining whether to perform the focus control process that moves the in-focus object plane position in the NEAR direction, or the focus control process that moves the in-focus object plane position in the FAR direction, based on whether or not the area information satisfies a given condition.

According to another aspect of the invention, there is provided a method for controlling a focus control device comprising:

acquiring a captured image that has been captured by an imaging section; and performing a focus control process that utilizes wobbling, wherein, when an in-focus object plane position that corresponds to a wobbling reference position lies between tissue and a treatment tool that is used to perform treatment on the tissue, the focus control process that utilizes the wobbling preferentially moves the in-focus object plane position in a first direction as compared with a second direction, the first direction being a direction toward the tissue with respect to the in-focus object plane position that corresponds to the wobbling reference position, and the second direction being a direction toward the treatment tool with respect to the in-focus object plane position that corresponds to the wobbling reference position.

BRIEF DESCRIPTION OF THE DRAWINGS

FIG. 4 illustrates a configuration example of an image sensor.

FIG. 12 is a flowchart illustrating an in-focus direction determination process.

FIGS. 13A to 13D illustrate an example of the positional relationship between tissue and a treatment tool, and an example of an in-focus direction determination result at each in-focus object plane position on a block basis.

FIGS. 14A to 14D illustrate an example of the positional relationship between a plurality of tissues and a treatment tool, and an example of an in-focus direction determination result at each in-focus object plane position on a block basis.

FIGS. 15A and 15B illustrate a specific example of a situation in which a plurality of tissues that differ in distance from an imaging section are captured.

FIGS. 17A to 17D illustrate an example of the positional relationship between tissue and a treatment tool in a needle-suture mode, and an example of an in-focus direction determination result at each in-focus object plane position on a block basis.

DESCRIPTION OF EXEMPLARY EMBODIMENTS

Figure 1:
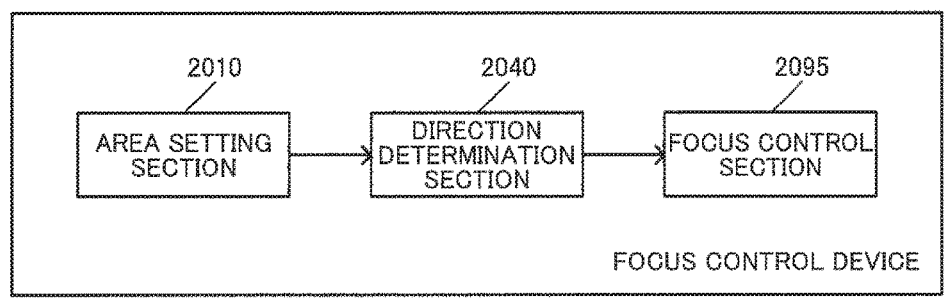
FIG. 1 illustrates a configuration example of a focus control device according to one embodiment of the invention.
Figure 2:
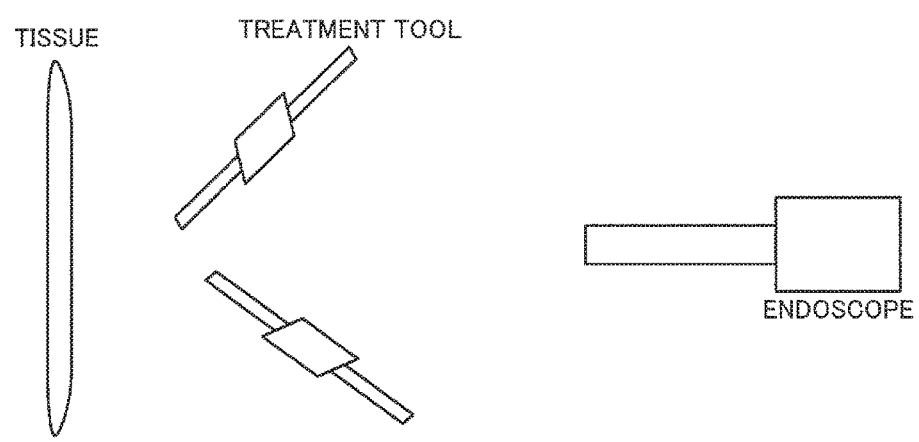
FIG. 2 illustrates an example of the positional relationship between an endoscope apparatus (imaging section) and a plurality of objects.

According to one embodiment of the invention, there is provided a focus control device comprising:

a processor comprising hardware, the processor being configured to implement:

an area setting process that sets a plurality of areas to a captured image that has been captured by an imaging section, each of the plurality of areas including a plurality of pixels;

a direction determination process that determines whether a target in-focus position lies in a NEAR direction or a FAR direction with respect to a reference position with respect to some or all of the plurality of areas set to the captured image to calculate a direction determination result with respect to each of the plurality of areas, the target in-focus position being a target of an in-focus object plane position; and a focus control process that preferentially brings an area among the plurality of areas that is situated away from the imaging section into focus based on the direction determination result, wherein the processor calculates at least one of area information about an area for which it has been determined that the target in-focus position lies in the NEAR direction, and the area information about an area for which it has been determined that the target in-focus position lies in the FAR direction, based on the direction determination result, and determines whether to perform the focus control process that moves the in-focus object plane position in the NEAR direction, or the focus control process that moves the in-focus object plane position in the FAR direction, based on whether or not the area information satisfies a given condition.

According to another embodiment of the invention, there is provided a focus control device comprising:

a processor comprising hardware, the processor being configured to implement:

an area setting process that sets a plurality of areas to a captured image that has been captured by an imaging section, each of the plurality of areas including a plurality of pixels;

a direction determination process that determines whether a target in-focus position lies in a NEAR direction or a FAR direction with respect to a reference position with respect to some or all of the plurality of areas set to the captured image to calculate a direction determination result with respect to each of the plurality of areas, the target in-focus position being a target of an in-focus object plane position; and a focus control process that preferentially brings an area among the plurality of areas that is situated away from the imaging section into focus based on the direction determination result, wherein the processor calculates an AF evaluation value with respect to each of the plurality of areas from a plurality of the captured images that include a first captured image and a second captured image, and implements the direction determination process based on a comparison process performed on the AF evaluation value calculated from the first captured image and the AF evaluation value calculated from the second captured image, the first captured image being an image captured in a state in which the in-focus object plane position lies in the NEAR direction with respect to the reference position, and the second captured image being an image captured in a state in which the in-focus object plane position lies in the FAR direction with respect to the reference position.

According to another embodiment of the invention, there is provided a focus control device comprising:

a processor comprising hardware, the processor being configured to implement:

an image acquisition process that acquires a captured image that has been captured by an imaging section; and a focus control process that utilizes wobbling, wherein, when an in-focus object plane position that corresponds to a wobbling reference position lies between tissue and a treatment tool that is used to perform treatment on the tissue, the processor implements the focus control process that utilizes the wobbling that preferentially moves the in-focus object plane position in a first direction as compared with a second direction, the first direction being a direction toward the tissue with respect to the in-focus object plane position that corresponds to the wobbling reference position, and the second direction being a direction toward the treatment tool with respect to the in-focus object plane position that corresponds to the wobbling reference position.

According to another embodiment of the invention, there is provided an endoscope apparatus comprising one of the above focus control device.

According to another embodiment of the invention, there is provided a method for controlling a focus control device comprising:

setting a plurality of areas to a captured image that has been captured by an imaging section, each of the plurality of areas including a plurality of pixels;

performing a direction determination process that determines whether a target in-focus position lies in a NEAR direction or a FAR direction with respect to a reference position with respect to some or all of the plurality of areas set to the captured image to calculate a direction determination result with respect to each of the plurality of areas, the target in-focus position being a target of an in-focus object plane position;

performing a focus control process that preferentially brings an area among the plurality of areas that is situated away from the imaging section into focus based on the direction determination result; and calculating at least one of area information about an area for which it has been determined that the target in-focus position lies in the NEAR direction, and the area information about an area for which it has been determined that the target in-focus position lies in the FAR direction, based on the direction determination result, and determining whether to perform the focus control process that moves the in-focus object plane position in the NEAR direction, or the focus control process that moves the in-focus object plane position in the FAR direction, based on whether or not the area information satisfies a given condition.

According to another embodiment of the invention, there is provided a method for controlling a focus control device comprising:

acquiring a captured image that has been captured by an imaging section; and performing a focus control process that utilizes wobbling, wherein, when an in-focus object plane position that corresponds to a wobbling reference position lies between tissue and a treatment tool that is used to perform treatment on the tissue, the focus control process that utilizes the wobbling preferentially moves the in-focus object plane position in a first direction as compared with a second direction, the first direction being a direction toward the tissue with respect to the in-focus object plane position that corresponds to the wobbling reference position, and the second direction being a direction toward the treatment tool with respect to the in-focus object plane position that corresponds to the wobbling reference position.

The exemplary embodiments of the invention are described below. Note that the following exemplary embodiments do not in any way limit the scope of the invention laid out in the claims. Note also that all of the elements described below in connection with the exemplary embodiments should not necessarily be taken as essential elements of the invention.

1. Method

A method used in connection with the embodiments of the invention is described below. A captured image may normally include an object that serves as an obstacle in addition to an object that is of interest to the user (i.e., an object to which the user is paying attention). In such a case, it is desirable that the object that is of interest to the user be easily observed (i.e., be brought into focus) within the captured image. However, the object that is of interest to the user is not necessarily brought into focus when an autofocus (AF) process is used in a simple way. For example, when a contrast AF process is used, a treatment tool may be brought into focus although the user is paying attention to tissue, since an area having high contrast is brought into focus. When a phase detection AF process is used, for example, it is possible to acquire information (e.g., lens moving amount) for achieving an in-focus state at each point at which phase difference information can be acquired. In this case, however, it is necessary to separately take account of a point that is of interest to the user.

It is possible to accurately bring the desired object into focus by utilizing a method that prompts the user to designate an object that serves as an obstacle (e.g., the method disclosed in JP-A-2006-245792). However, the state of the obstacle within the captured image may frequently change in a given situation. In such a case, since the user must designate the obstacle each time the state of the obstacle has changed, the burden imposed on the user increases.

For example, when an endoscopic procedure (e.g., laparoscopic surgery) is performed, a treatment tool is inserted into a body together with a scope (imaging section), and a treatment on tissue is performed using the treatment tool. The treatment tool is a tool that is used for the treatment on tissue. Specific examples of the treatment tool include an energy device such as an electrosurgical knife, forceps, and the like. Since the treatment tool is used for the treatment on tissue (e.g., membrane-like tissue is pulled upward using forceps, or tissue secured using forceps is excised using an electrosurgical knife), the treatment tool is frequently moved by the user (doctor or operator). Therefore, the position and the size of the treatment tool within the captured image change frequently. Specifically, since an area in which an obstacle is captured frequently changes in a case where the user is paying attention to tissue and a treatment tool serves as an obstacle, and a case where the user is paying attention to a treatment tool and tissue serves as an obstacle, the burden imposed on the user increases if the user must manually designate an obstacle.

If an object that is of interest to the user can be automatically determined within the captured image, it is possible to bring the object into focus by performing an AF process using information about an area in which the object is captured.

The invention proposes the focus control device described below. As illustrated in FIG. 1, a focus control device according to one embodiment of the invention includes an area setting section 2010 that sets a plurality of areas to a captured image that has been captured by an imaging section (that corresponds to the imaging section 200 illustrated in FIG. 3 (described later)), each of the plurality of areas including a plurality of pixels, a direction determination section 2040 that performs a direction determination process that determines whether a target in-focus position lies in a NEAR direction or a FAR direction with respect to a reference position with respect to each of the plurality of areas set to the captured image to calculate a direction determination result with respect to each of the plurality of areas, the target in-focus position being a target of an in-focus object plane position, and a focus control section 2095 that performs a focus control process that preferentially brings an area among the plurality of areas that is situated away from the imaging section into focus based on the direction determination result.

Figure 3:
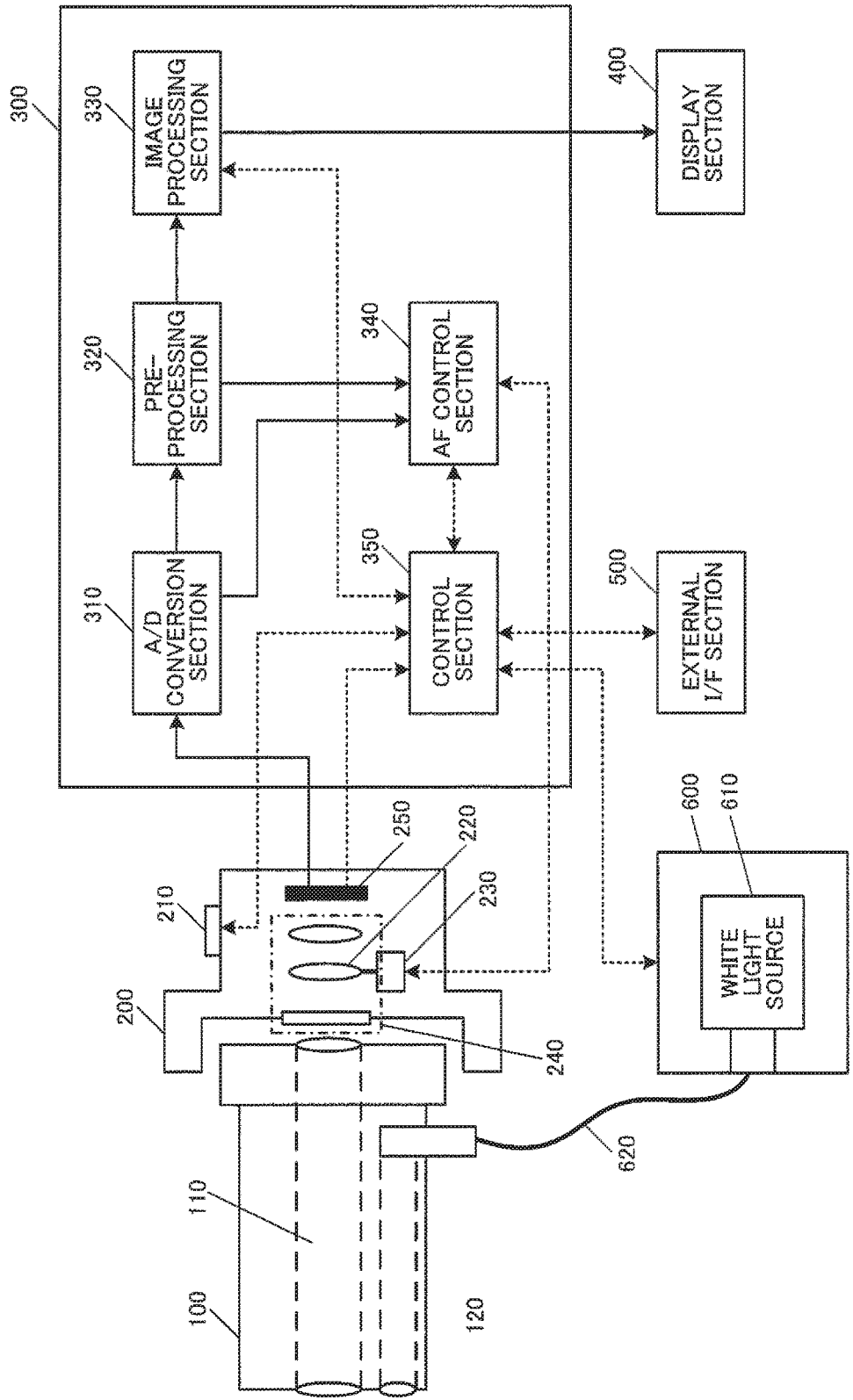
FIG. 3 illustrates a configuration example of an endoscope apparatus that includes a focus control device according to one embodiment of the invention.

The term "in-focus object plane position" used herein refers to the position of an object when a system that includes an optical system (i.e., the objective lens system 240 illustrated in FIG. 3 (described later) in a narrow sense), an image plane (i.e., the plane of the image sensor 250 illustrated in FIG. 3), and an object is in an in-focus state. For example, when the image sensor 250 illustrated in FIG. 3 (described later) is stationary, and the focus lens 220 included in the optical system is movable, the in-focus object plane position is determined by determining the position of the focus lens 220. In this case, a captured image in which an object that lies within the depth of field including the in-focus object plane position is brought into focus, is acquired.

The terms "NEAR", "NEAR direction", "FAR", and "FAR direction" used herein refer to the direction in which the target in-focus position lies with respect to the reference position. The target in-focus position lies in the NEAR direction with respect to the reference position when the target in-focus position lies on the side of the imaging section 200 (optical system and image sensor 250) with respect to the reference position, and the target in-focus position lies in the FAR direction with respect to the reference position when the target in-focus position lies opposite to the imaging section 200 with respect to the reference position. When the in-focus object plane position can be controlled by changing the position of the focus lens 220 (see FIG. 3), for example, the in-focus object plane position can be moved in the NEAR direction by moving the position of the focus lens 220 toward the near point (WIDE end), and can be moved in the FAR direction by moving the position of the focus lens 220 toward the far point (TELE end).

The expression "preferentially brings an area that is situated away from the imaging section into focus" used herein means that, when the captured image includes a first object that is situated at a distance D1 from the imaging section 200, and a second object that is situated at a distance D2 (<D1) from the imaging section 200, for example, it is likely that the first object is brought into focus as compared with the second object. This process can be implemented by preferentially moving the in-focus object plane position in the FAR direction. For example, when an evaluation value pF in the FAR direction and an evaluation value pN in the NEAR direction are acquired as the direction determination result, and the in-focus object plane position is moved in the FAR direction when pF>thF has been satisfied, and is moved in the NEAR direction when pN>thN has been satisfied, the above control process may be designed so that pF>thF is easily satisfied, and pN>thN is not easily satisfied. Specifically, the threshold values may be set so that thF<thN. When the evaluation value is the ratio with respect to all of the effective blocks (as described later), pF+pN=100(%). In this case, the threshold values may be set so that thF<50(%)<thN (=100-thF). Specifically, when the sum of the evaluation values is fixed, the threshold value may be set to be a value that is biased in the FAR direction instead of setting the threshold value to be an intermediate value (i.e., half of the sum of the evaluation values) to implement the above control process.

This makes it possible to bring an appropriate object into focus when it is likely that the user is paying attention to an object that is situated away from the imaging section 200. For example, when the method is applied to an endoscopic procedure, the captured image is an in vivo image in which a spatially restricted area is captured. It is considered that the user (e.g., scopist) operates the imaging section 200 so that the desired object can be easily observed. For example, the user moves the imaging section 200 so as to directly face the tissue of interest. Therefore, the tissue (i.e., object) of interest occupies a certain area within the captured image, and it is unlikely that an object other than the tissue lies behind the tissue (so as to be situated further away from the imaging section 200). Specifically, the object of interest is situated farthest (or almost farthest) within the captured image. Since the user performs an endoscopic procedure while observing the captured image, a treatment tool or the like that serves as an obstacle may be captured in front of the tissue (so as to be situated closer to the imaging section 200). However, since the tissue is preferentially brought into focus instead of the treatment tool, it is possible to prevent a situation in which the treatment tool is brought into focus.

Although it is likely that an object that is situated farthest (situated at the deepest position) is the object of interest to the user when the focus control device according to the embodiments of the invention is used (see above), the user may pay attention to another object. For example, when the user performs suture, the user must hold a needle and a suture at an appropriate angle using forceps or the like. In this case, the user normally pays attention to the needle and the suture that are situated in front of the tissue, instead of the tissue. There may also be a case where tissue that is situated on the front side is the object of interest, as described later with reference to FIGS. 15A and 15B in which membrane-like tissue is moved upward for treatment.

Specifically, the focus control process according to the embodiments of the invention basically preferentially brings an area that is situated away from the imaging section 200 into focus, but may be performed according to a different principle when an exception condition has been satisfied. For example, a needle or a suture may be brought into focus by bringing an object that is situated close to the imaging section 200 into focus, or an object that is situated relatively on the front side may be brought into focus by bringing an object that is other than a treatment tool and has a large area into focus.

The embodiments of the invention are described in detail below. The focus control device according to the embodiments of the invention, and a system configuration example of an endoscope apparatus that includes the focus control device will be described first, and the flow of the process according to the embodiments of the invention will then be described using flowcharts. A specific example according to the embodiments of the invention will be described thereafter taking a specific situation as an example.

2. System Configuration Example

An endoscope apparatus (endoscope system) according to one embodiment of the invention is described below with reference to FIG. 3. The endoscope system according to one embodiment of the invention includes a rigid scope 100 that is inserted into a body, an imaging section 200 that is connected to the rigid scope 100, a processing section 300, a display section 400, an external I/F section 500, and a light source section 600.

The light source section 600 includes a white light source 610 that emits white light, and a light guide cable 620 that guides the light emitted from the white light source 610 to the rigid scope.

The rigid scope 100 includes a lens system 110 that includes an imaging lens, a relay lens, an eyepiece, and the like, and a light guide section 120 that guides the light emitted from the light guide cable 620 to the end of the rigid scope.

The imaging section 200 includes an objective lens system 240 that forms an image of the light emitted from the lens system 110. The objective lens system 240 includes a focus lens 220 that adjusts the in-focus object plane position. The imaging section 200 also includes an image sensor 250 that photoelectrically converts the reflected light focused by the objective lens system 240 to generate an image, a focus lens driver section 230 that drives the focus lens 220, and an AF button (AF start/stop button) 210 that controls AF start/stop. The focus lens driver section 230 is implemented by a voice coil motor (VCM), for example.

The details of the image sensor 250 according to one embodiment of the invention are described below with reference to FIG. 4. FIG. 4 is a partially enlarged view illustrating the image sensor 250. As illustrated in FIG. 4, the image sensor 250 has a structure in which a plurality of pixels are arranged in a two-dimensional array, and R, G, and B color filters are disposed in a Bayer array on a pixel basis. The image sensor 250 may be an arbitrary image sensor other than an image sensor having a Bayer color filter array (see FIG. 4), such as an image sensor that utilizes a complementary color filter, a stacked image sensor that is designed so that each pixel can receive light having a different wavelength without using a color filter, and a monochrome image sensor that does not utilize a color filter, as long as the object can be captured to obtain an image.

The processing section 300 includes an A/D conversion section 310, a pre-processing section 320, an image processing section 330, an AF control section 340, and a control section 350. The A/D conversion section 310 converts an analog signal sequentially output from the image sensor 250 into a digital image, and sequentially outputs the digital image to the pre-processing section 320. The pre-processing section 320 performs image processing (e.g., white balance process and interpolation process (demosaicing process)) on the image output from the AD conversion section 310, and sequentially outputs the resulting image to the image processing section 330 and the AF control section 340. The image processing section 330 performs image processing (e.g., color conversion process, grayscale transformation process, edge enhancement process, scaling process, and noise reduction process) on the image output from the pre-processing section 320, and sequentially outputs the resulting image to the display section 400.

The AF control section 340 includes an area setting section 2010, a mode setting section 2020, a block AF evaluation value calculation section 2030, a direction determination section (block direction determination section) 2040, a reliability calculation section 2050, a block feature quantity calculation section 2060, a null block setting section 2070, a null frame setting section 2075, an in-focus direction determination section 2080, and a focus lens control section 2090.

The area setting section 2010 sets a plurality of areas used for the AF process to the captured image. The plurality of areas include both an AF area and an evaluation block. The mode setting section 2020 sets an AF mode. The block AF evaluation value calculation section 2030 calculates an evaluation value used for the AF process on an evaluation block basis. The direction determination section 2040 determines the direction of the target in-focus position (in-focus direction) on an evaluation block basis based on the evaluation value. The direction determination result is information that represents the NEAR direction or the FAR direction in a narrow sense. The reliability calculation section 2050 calculates reliability on an evaluation block basis, the reliability representing the probability that the direction determination result is reliable. The block feature quantity calculation section 2060 calculates a feature quantity on an evaluation block basis. The null block setting section 2070 sets a null block based on the feature quantity. The term "null block" used herein refers to an evaluation block that is not used for the in-focus direction determination process. The null frame setting section 2075 determines whether or not to set the processing target frame to be a null frame. The term "null frame" used herein refers to a frame that is not used for the in-focus direction determination process. The in-focus direction determination section 2080 determines the in-focus direction (i.e., the moving direction of the in-focus object plane position (or the moving direction of the focus lens 220 that corresponds to the moving direction of the in-focus object plane position)). The focus lens control section 2090 moves the focus lens 220 in a direction that corresponds to the determined in-focus direction.

Figure 5:
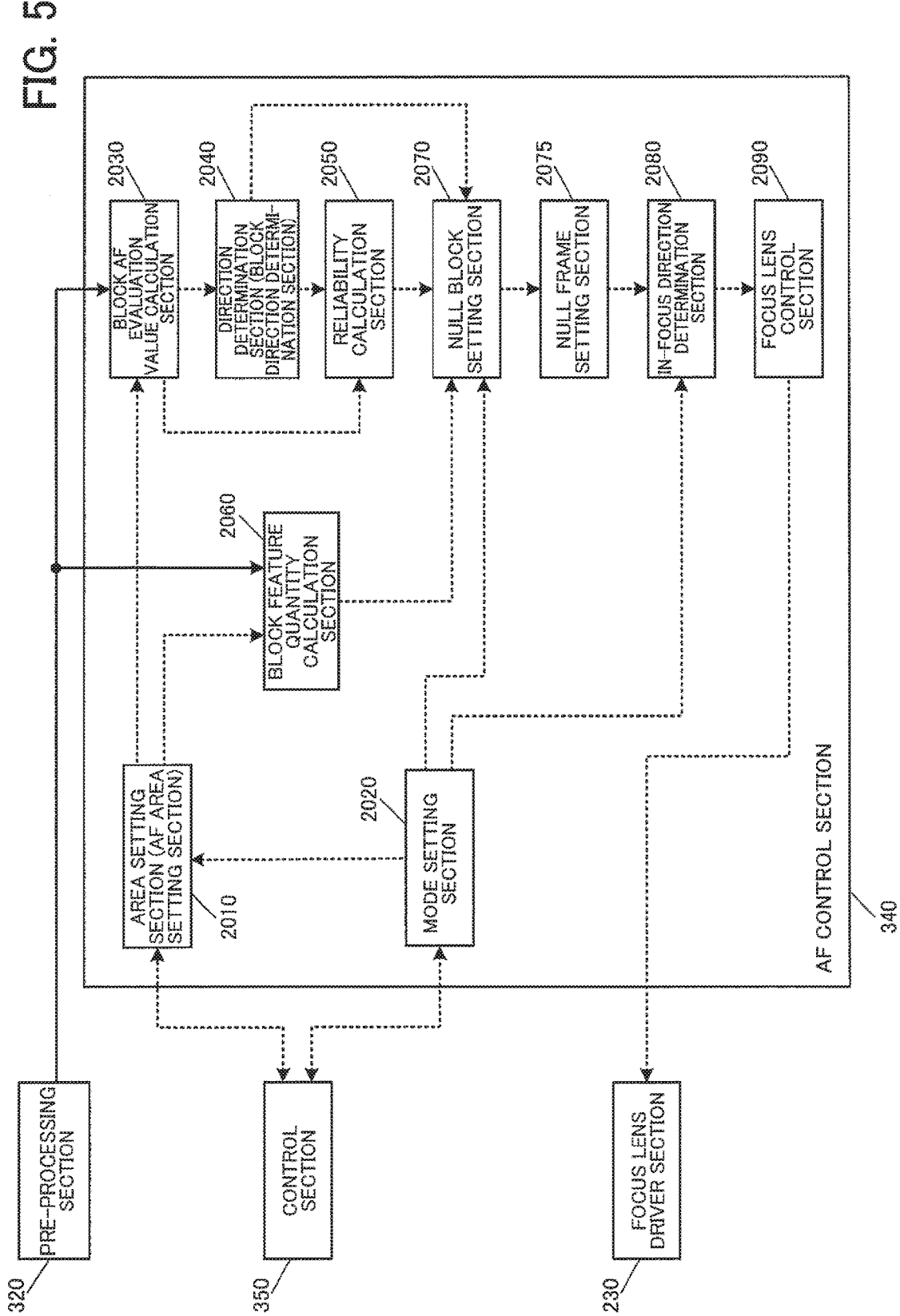
FIG. 5 illustrates a configuration example of an AF control section.

Note that the details of the process performed by each section of the AF control section 340 are described later. The focus control section 2095 illustrated in FIG. 1 may correspond to the configuration of the AF control section 340 illustrated in FIG. 5 excluding the area setting section 2010 and the direction determination section 2040, for example. The focus control device according to one embodiment of the invention may correspond to the AF control section 340 illustrated in FIG. 5. Note that the configuration of the focus control device is not limited thereto. Various modifications and variations may be made (e.g., the entire processing section 300 illustrated in FIG. 1 may be used as the focus control device). Some of the elements included in the focus control device may be omitted, or an additional element may be provided to the focus control device, for example. Various modifications and variations may also be made of the configuration illustrated in FIG. 3 and the like.

The control section 350 is connected to the external I/F section 500, the image processing section 330, the AF control section 340, the image sensor 250, the AF button 210, and the like, and exchanges a control signal with the external I/F section 500, the image processing section 330, the AF control section 340, the image sensor 250, the AF button 210, and the like.

The display section 400 is a liquid crystal monitor, for example. The display section 400 displays the image sequentially output from the image processing section 330.

The external I/F section 500 is an interface that allows the user to perform an input operation and the like on the endoscope apparatus. For example, the external I/F section 500 includes a mode button that is used to switch the AF mode, a setting button that is used to set the position and the size of the AF area, an adjustment button that is used to adjust the parameter of image processing, and the like. The endoscope system according to one embodiment of the invention has a tissue mode (i.e., AF mode) in which tissue is brought into focus, and a needle-suture mode (i.e., AF mode) in which a needle and a suture used for an endoscopic procedure are brought into focus.

3. Process Flow

An outline of the AF control process that is performed by the AF control section 340 according to one embodiment of the invention is described below with reference to FIG. 6. When the user has operated the AF button 210 to start the AF process, the AF control section 340 starts a focus operation.

The AF control section 340 causes the focus lens to make a wobbling motion in synchronization with the acquisition timing of the image sequentially output from the A/D conversion section 310. The AF control section 340 determines the in-focus direction based on the image acquired while the focus lens makes a wobbling motion (S100). The details of the in-focus direction determination process (S100) are described later. The AF control section 340 changes the wobbling center position based on the in-focus direction determined by the step S100 (S110). The in-focus direction determined by the step S100 is "NEAR", "FAR", or "UNMOVING" (described later). When the in-focus direction has been determined to be "NEAR direction", the AF control section 340 moves the wobbling center position by a given amount in the direction in which the in-focus object plane position is situated close to the image sensor 250. When the in-focus direction has been determined to be "FAR direction", the AF control section 340 moves the wobbling center position by a given amount in the direction in which the in-focus object plane position is situated away from to the image sensor 250. When the in-focus direction has been determined to be "UNMOVING direction", the AF control section 340 does not change the wobbling center position.

The AF control section 340 determines whether or not the object has been brought into focus (S120). The AF control section 340 may determine whether or not the object has been brought into focus by performing a known in-focus determination process, for example. When the object has not been brought into focus, the AF control section 340 performs the step S100 again, and gradually brings the wobbling center position closer to the in-focus position. When the object has not been brought into focus, the AF control section 340 stops causing the focus lens 220 to make a wobbling motion, and terminates the focus operation.

When the AF control section 340 has terminated the focus operation, the AF control section 340 starts a standby operation. Specifically, the AF control section 340 detects a change in scene (S130). The AF control section 340 detects a change in scene by monitoring a change in the color or the brightness of an image, the motion of an image, and the like using the image sequentially output from the pre-processing section 320, for example. The AF control section 340 determines whether or not a change in scene has been detected (S140). When a change in scene has not been detected, the AF control section 340 performs the step S130 again. When a change in scene has been detected, the AF control section 340 terminates the standby operation. When the AF control section 340 has terminated the standby operation, the AF control section 340 resumes the focus operation. Note that the AF control section 340 fixes the focus lens position at a position when the focus operation has been terminated (i.e., does not drive the focus lens 220) during the standby operation, for example.

Figure 7:
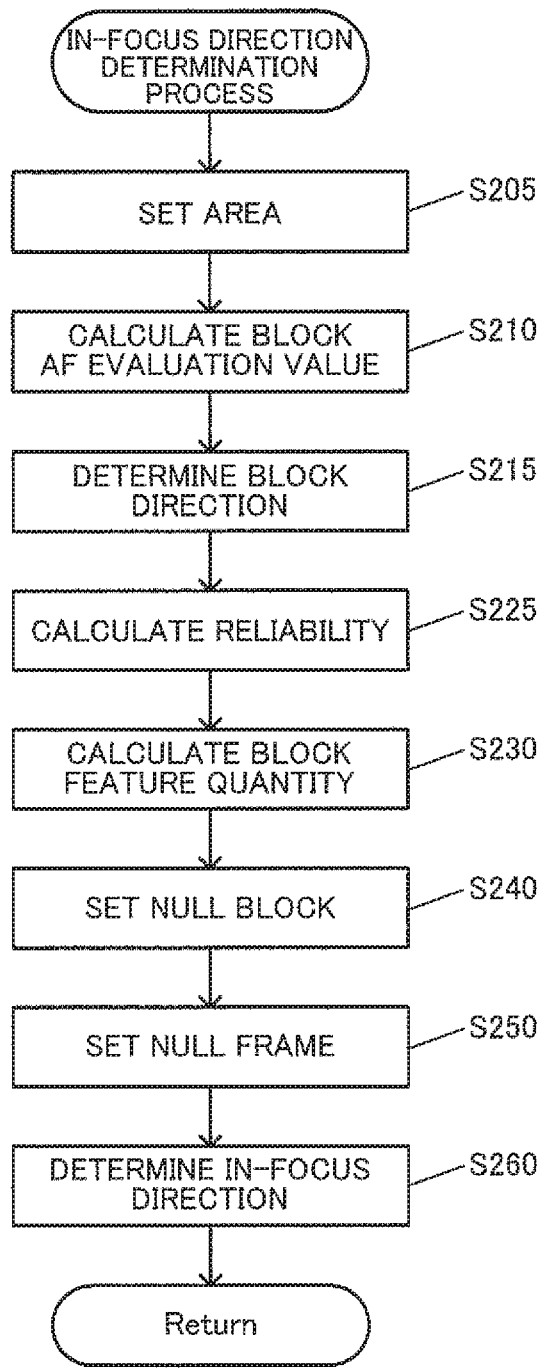
FIG. 7 is a flowchart illustrating an in-focus direction determination process.

The details of the in-focus direction determination process (S100) performed by the AF control section 340 are described below with reference to FIG. 7.

In one embodiment of the invention, the tissue mode and the needle-suture mode are provided as the AF mode. For example, the control section 350 sets the AF mode to the mode setting section 2020 corresponding to information input from the external OF section 500. The image data (captured image) that has been captured by the image sensor 250 may be analyzed by the control section 350, and the AF mode may be changed based on a specific image pattern, motion, and the like. The mode setting section 2020 outputs AF mode information that represents the tissue mode or the needle-suture mode to the area setting section (AF area setting section) 2010, the null block setting section 2070, and the in-focus direction determination section 2080.

Figure 8A:
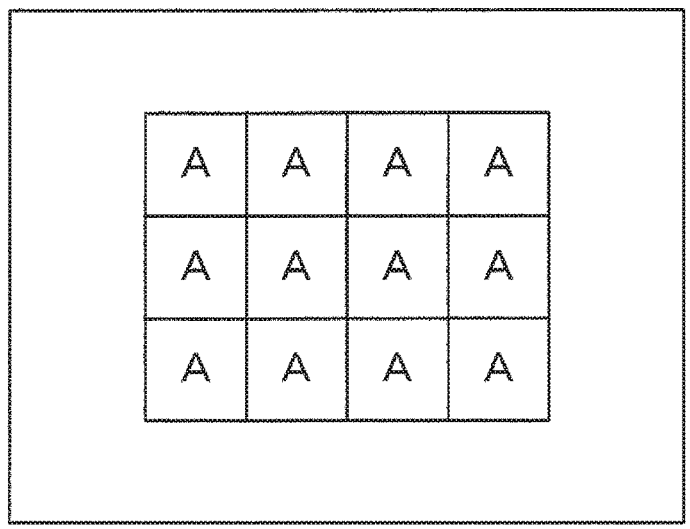
FIGS. 8A and 8B are views illustrating an area setting example corresponding to a mode.
Figure 8B:
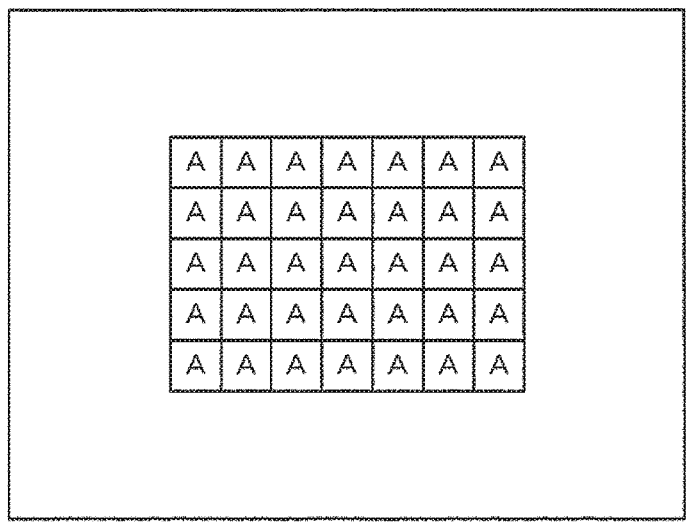

The area setting section 2010 sets an AF area that includes a plurality of blocks to the image based on information (e.g., information about the position and the size of the AF area) output from the control section 350 (S205). FIGS. 8A and 8B illustrate an AF area setting example. In the example illustrated in FIGS. 8A and 8B, the outer rectangle represents the entire image, and each rectangle indicated by A represents an evaluation block that is an area for which the AF evaluation value, the reliability, and the like are calculated (as described later). In the example illustrated in FIGS. 8A and 8B, the AF area is a range that includes all of the evaluation blocks. In the example illustrated in FIG. 8A, twelve (4×3) evaluation blocks are set to a center area of the image (image data). In the example illustrated in FIG. 8B, thirty-five (7×5) evaluation blocks are set to a center area of the image.

When the AF mode has been set to the tissue mode, the area setting section 2010 sets the evaluation blocks as illustrated in FIG. 8A corresponding to the AF mode information output from the mode setting section 2020. When the AF mode has been set to the needle-suture mode, the area setting section 2010 sets the evaluation blocks as illustrated in FIG. 8B so as to be smaller than those set in the tissue mode since the target object (i.e., needle and suture) is smaller than tissue. Since a needle and a suture are normally manipulated in a center area of the screen, the AF area is set to be smaller than that set in the tissue mode. Since a needle and a suture are normally captured at a position lower to some extent than the center of the image due to the effect of gravity, the evaluation blocks may be set at a position lower than the center of the image (image data) instead of setting the AF area in a center area of the image (image data) (see FIG. 8B) so that an area that includes a needle and a suture is reliably included within the AF area. The evaluation blocks need not necessarily be contiguous to each other, and may differ in size, shape, and the like. The size, the shape, and the like of the evaluation blocks may be appropriately changed corresponding to the object, the operation performed by the user, and the like. The evaluation blocks need not necessarily be changed corresponding to the mode. For example, identical evaluation blocks may be set in the tissue mode and the needle-suture mode. The area setting section 2010 outputs area setting information to the block AF evaluation value calculation section 2030 and the block feature quantity calculation section 2060.

The block AF evaluation value calculation section 2030 calculates the AF evaluation value with respect to each evaluation block set by the area setting section 2010 based on the pixel value of the image data output from the pre-processing section 320 (S210). The AF evaluation value is increased corresponding to the degree of in-focus with respect to the object within the block.

The AF evaluation value can be calculated based on the frequency characteristics, the brightness distribution characteristics, and the like of the object captured within each evaluation block. For example, when a band-pass filter is applied to each pixel of the image of each evaluation block, and the output value is accumulated (integrated), a larger value is obtained as the contrast of the image of each evaluation block increases corresponding to the frequency characteristics of the band-pass filter. For example, when a brightness histogram (i.e., brightness distribution characteristics) of the image of each evaluation block is calculated, a larger value is obtained as the contrast of the image of each evaluation block increases corresponding to the distribution range, the dispersion, the standard deviation, and the like of the histogram.

The AF evaluation value may be calculated based on object distance information about each evaluation block that has been acquired using a known method (e.g., phase difference method, pattern projection method, and light field method).

The block AF evaluation value calculation section 2030 outputs the AF evaluation value with respect to each evaluation block (that has been calculated as described above) to the direction determination section 2040 and the reliability calculation section 2050.

The direction determination section 2040 determines the in-focus direction with respect to each evaluation block from the AF evaluation value with respect to each evaluation block output from the block AF evaluation value calculation section 2030 (S215). More specifically, the direction determination section 2040 compares the AF evaluation values with respect to each evaluation block that have been calculated from an image captured when the focus lens has moved in the NEAR direction due to the wobbling motion, and an image captured when the focus lens has moved in the FAR direction due to the wobbling motion, and determines the direction in which the AF evaluation value is larger to be the in-focus direction with respect to each evaluation block. Note that the NEAR direction is a direction in which the in-focus object plane position moves closer to the image sensor 250, and the FAR direction is a direction (infinity direction) in which the in-focus object plane position moves away from the image sensor 250. The in-focus direction determination result with respect to each evaluation block is represented by a binary value (NEAR or FAR). Note that the in-focus direction determination result may be output using a ternary value or the like taking account of the magnitude of the AF evaluation value and the like. When wobbling is performed in the vicinity of an in-focus state, the AF evaluation values with respect to each evaluation block that have been calculated from an image captured when the focus lens has moved in the NEAR direction, and an image captured when the focus lens has moved in the FAR direction, may be equal to each other. In such a case, the direction determined using the preceding frame with respect to such a block is output as the in-focus direction with respect to the evaluation block. Note that the expression "the AF evaluation values are equal to each other" includes a case where the difference between the AF evaluation values is smaller than a given threshold value.

The direction determination section 2040 outputs the direction determination result with respect to each evaluation block to the reliability calculation section 2050 and the null block setting section 2070.

The reliability calculation section 2050 calculates the reliability of each evaluation block based on the AF evaluation value with respect to each evaluation block output from the block AF evaluation value calculation section 2030, and the direction determination result with respect to each evaluation block output from the direction determination section 2040 (S225). Note that the reliability of each evaluation block is a measure that represents the probability that the direction determination result with respect to each evaluation block is reliable. For example, the change rate of the AF evaluation value in the time direction is calculated, and the reliability of the evaluation block is increased when the change rate falls within a given range. In this case, the reliability may be increased in proportion to the change rate. The reliability of the evaluation block is decreased when the change rate falls outside the given range. It is considered that the change rate is very small when the object does not have sufficient contrast, or the image is blurred to a large extent, for example, and a correct direction determination result has not been obtained. It is considered that the change rate is very large when the object captured within the image has changed due to the motion of the object, or a motion blur has occurred, for example, and a correct direction determination result has not been obtained.

Alternatively, the reliability may be calculated corresponding to the degree of dispersion of the direction determination result with respect to the evaluation block in the time direction (see FIG. 9) instead of calculating the reliability based on the AF evaluation value.

Figure 9:
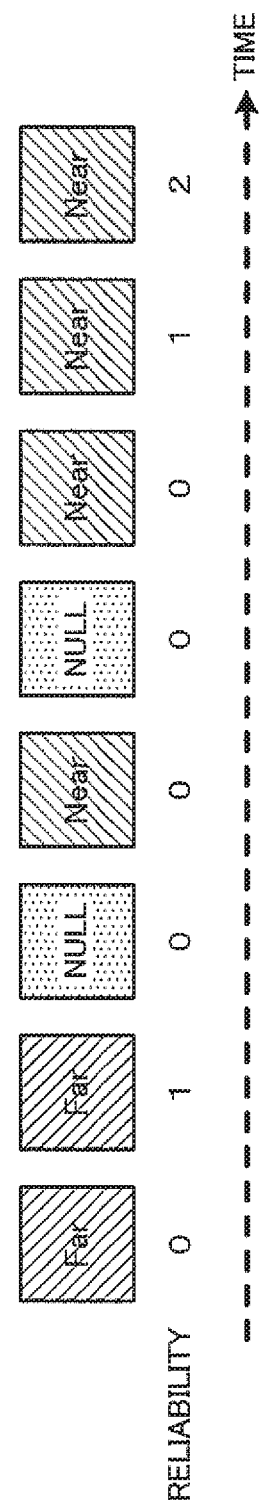
FIG. 9 is a view illustrating a method that calculates reliability based on a time-series change in direction determination result.

FIG. 9 illustrates an example in which direction determination results "FAR", "FAR", "NULL" (described later), "NEAR", "NULL", "NEAR", "NEAR", and "NEAR" have been sequentially obtained with respect to the evaluation block. For example, the number of direction determination results that are identical to each other and have been obtained consecutively may be counted, and a value that is proportional to the count value may be calculated to be the reliability with respect to the evaluation block. For example, the reliability that corresponds to the last timing at which the direction determination result was "NEAR" is "2", for example. The reliability calculation section 2050 outputs the reliability with respect to each block to the null block setting section 2070.

The block feature quantity calculation section 2060 calculates the feature quantity with respect to each evaluation block based on the image data output from the pre-processing section 320, and the AF area information output from the area setting section 2010 (S230). The block feature quantity is a quantity that characterizes the object captured within each evaluation block. For example, the block feature quantity is color information about each evaluation block. The block feature quantity calculation section 2060 outputs the calculated feature quantity to the null block setting section 2070.

The block feature quantity may be an arbitrary feature quantity (e.g., brightness, edge quantity, the temperature of the object obtained from a dedicated sensor (not illustrated in the drawings), and reflectivity with respect to narrow-band light) as long as at least whether or not the object is tissue can be determined.

The null block setting section 2070 sets a null block using the AF mode information output from the mode setting section 2020, the in-focus direction with respect to each evaluation block output from the direction determination section 2040, the feature quantity with respect to each evaluation block output from the block feature quantity calculation section 2060, the reliability with respect to each evaluation block output from the reliability calculation section 2050, and the like (S240).

Figure 10:
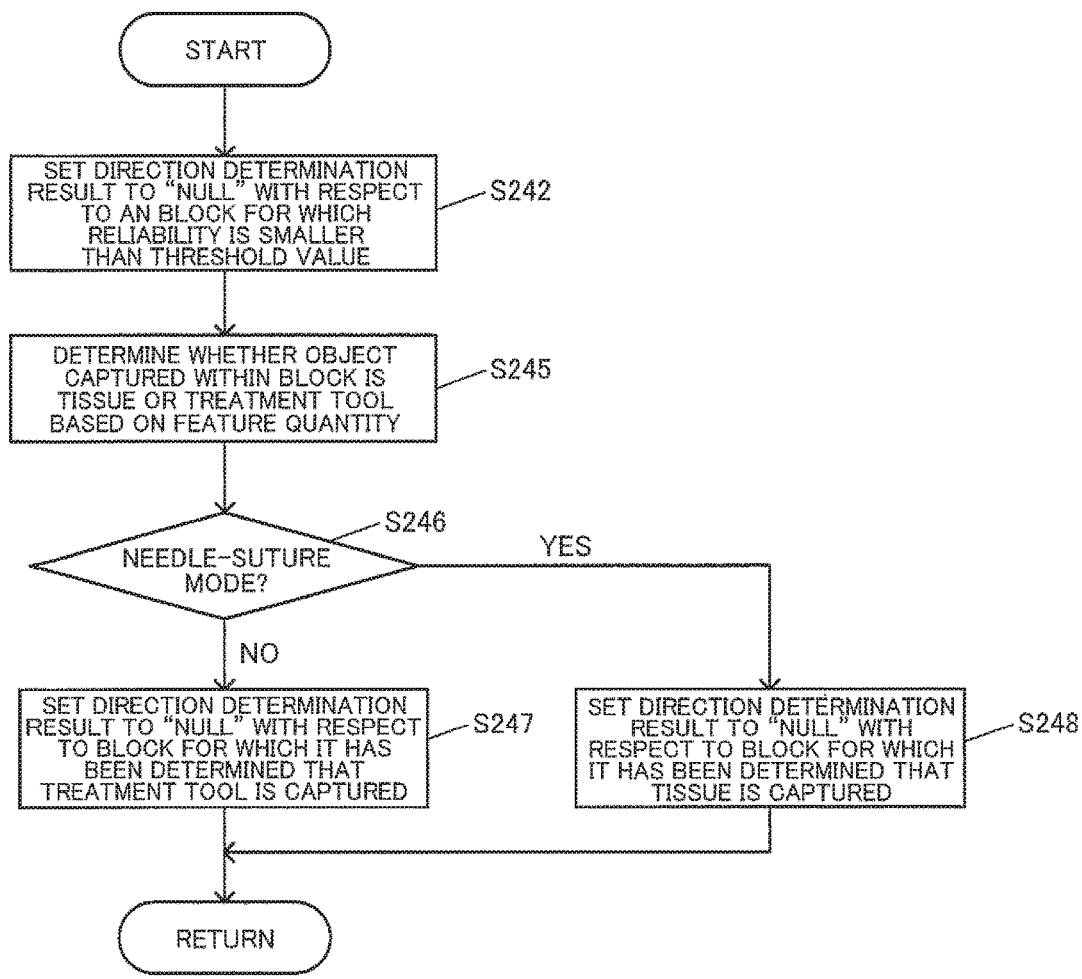
FIG. 10 is a flowchart illustrating a null block setting process.

FIG. 10 illustrates an example of the null block setting process (step S240) that is performed by the null block setting section 2070 with respect to each evaluation block.

The null block setting section 2070 performs a threshold value process on the reliability with respect to each evaluation block (S242). The null block setting section 2070 sets the direction determination result to "NULL" with respect to an evaluation block for which the reliability is smaller than a given threshold value. The null block setting section 2070 determines whether the object captured within each evaluation block is tissue or an object (e.g., treatment tool (e.g., forceps)) other than tissue using the block feature quantity of each evaluation block (S245).

The null block setting section 2070 determines whether or not the AF mode output from the mode setting section 2020 is the needle-suture mode (S246). When the null block setting section 2070 has determined that the AF mode is not the needle-suture mode in the step S246, the null block setting section 2070 sets the direction determination result to "NULL" with respect to each evaluation block for which it has been determined that the object captured therein is an object (e.g., treatment tool) other than tissue in the step S245 (S247).

When the null block setting section 2070 has determined that the AF mode is the needle-suture mode in the step S246, the null block setting section 2070 sets the direction determination result to "NULL" with respect to each evaluation block for which it has been determined that the object captured therein is tissue in the step S245 (S248).

It is possible to reduce the effect of an object other than the object of interest when the driving direction of the focus lens 220 is determined as described later, and accurately bring the object of interest into focus, by setting a block in which the object of interest is not captured to "NULL".

The null block setting section 2070 outputs the direction determination result with respect to each evaluation block to the null frame setting section 2075. The direction determination result output from the null block setting section 2070 is "NEAR", "FAR", or "NULL".

The null frame setting section 2075 sets a null frame based on the direction determination result with respect to each evaluation block output from the null block setting section 2070 (S250). Note that the term "frame" used herein refers to the entire image that is used during the in-focus direction determination process (S100). Therefore, the term "frame" is also used when the image sensor 250 or the like outputs an interlaced image. More specifically, when a plurality of fields are combined to form an image, the term "frame" used herein may refer to the image (frame in a narrow sense), or may refer to each of the plurality of fields.

Figure 11A:
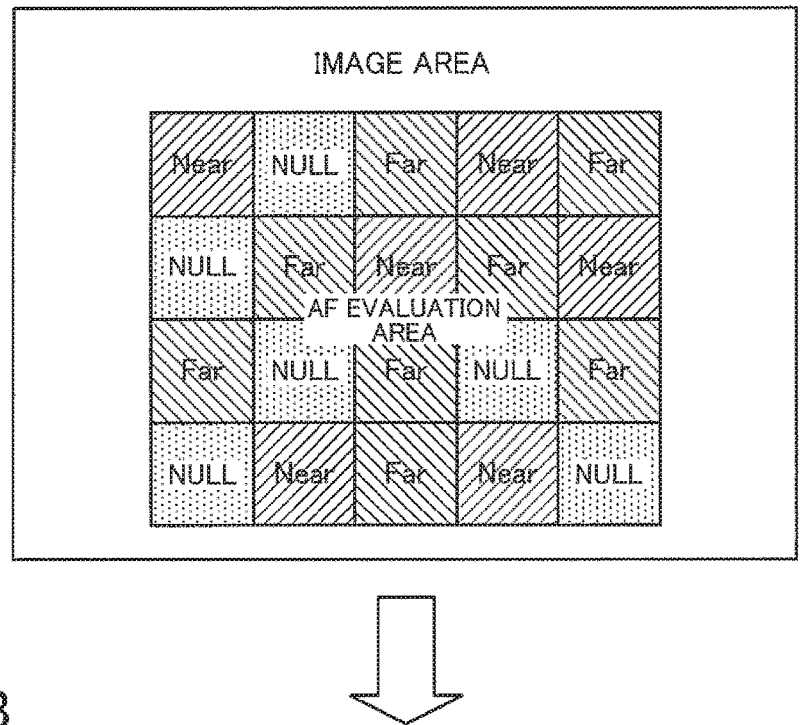
FIGS. 11A and 11B are views illustrating a method that sets a null frame from the dispersion of direction determination results.
Figure 11B:
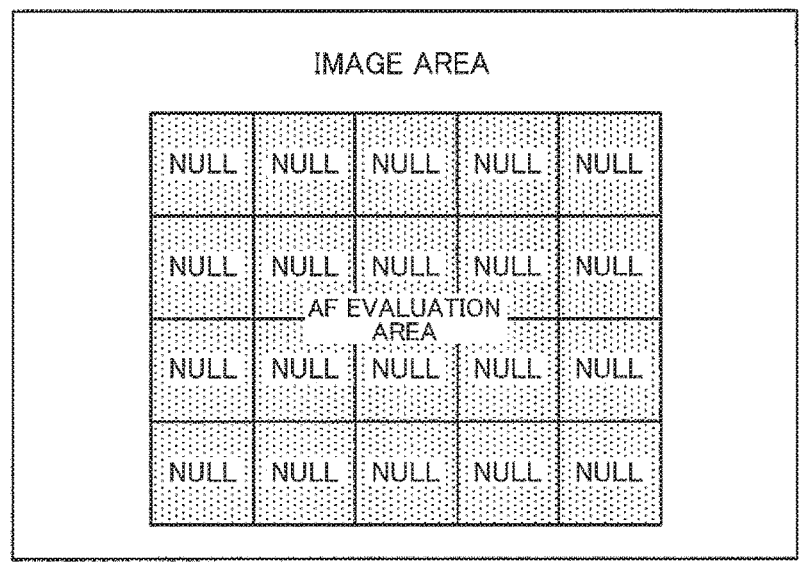

The null frame setting process is performed in order to reduce the possibility that the direction determination result with respect to each evaluation block varies due to the effect of mist generated during an endoscopic procedure, for example, and the focus lens is driven in an unintended direction. For example, the null frame setting process calculates the degree of dispersion of the direction determination result with respect to each evaluation block within the frame. For example, the direction determination result with respect to each evaluation block is compared with the direction determination result with respect to the adjacent evaluation block, the number of evaluation blocks for which it has been determined that the direction determination result is different are counted, and the total count with respect to each evaluation block is determined to be the degree of dispersion (see FIG. 11A). Specifically, the degree of dispersion increases when the adjacent evaluation blocks do not have the same direction determination result as each evaluation block. The degree of dispersion is compared with a given threshold value. When the degree of dispersion is larger than the given threshold value, it is determined that the direction determination result with respect to the frame is not reliable due to the effect of mist or the like, and the direction determination result with respect to each evaluation block is set to "NULL" (see FIG. 11B). Since the in-focus direction determination section 2080 (described below) makes a determination so as not to move the focus lens when all of the blocks are set to "NULL" (S279), it is possible to prevent a situation in which the focus lens is driven in an unintended direction. The null frame setting section 2075 outputs the direction determination result with respect to each block to the in-focus direction determination section 2080.

The in-focus direction determination section 2080 determines the final in-focus direction using the AF mode information output from the mode setting section 2020, and the in-focus direction determination result within respect to each evaluation block output from the null frame setting section 2075 (S260).

FIG. 12 illustrates an example of the focus lens driving direction determination process (step S260) performed by the in-focus direction determination section 2080. In FIG. 12, the evaluation block for which the direction determination result has not been determined to be null is referred to as "effective block". The number of effective blocks included in the AF area is counted (S262). When it has been determined in a step S264 that the number of effective blocks is equal to or smaller than a given threshold value, it is determined that the frame of interest is not reliable, and the in-focus direction is set to "UNMOVING" (S279).

When it has been determined in the step S264 that the number of effective blocks is larger than the given threshold value, the number of evaluation blocks for which it has been determined that the direction determination result is the NEAR direction (hereinafter referred to as "NEAR blocks") is counted (S265), and the ratio of the number of NEAR blocks with respect to the total number of effective blocks is calculated (S266).

In a step S270, whether or not the AF mode information output from the mode setting section 2020 represents the needle-suture mode is determined. When the AF mode information represents the needle-suture mode, a step S273 is performed. When the AF mode information represents a mode (tissue mode) other than the needle-suture mode, a step S272 is performed.

In the step S272, a threshold value process is performed using a given threshold value. Since the position of tissue lies in the FAR direction with respect to the position of a treatment tool, the in-focus object plane position is preferentially moved in the FAR direction in the tissue mode. In order to preferentially move the in-focus object plane position in the FAR direction, the threshold value M used in the step S272 is set to be equal to or larger than half of the number of effective blocks (e.g., equal to or larger than 60% of the number of effective blocks). When the ratio of the number of NEAR blocks with respect to the total number of effective blocks is larger than the threshold value, the in-focus direction is set to "NEAR" (S276). When the ratio of the number of NEAR blocks with respect to the total number of effective blocks is equal to or smaller than the threshold value, the in-focus direction is set to "FAR" (S275).

In the step S273, a threshold value process is performed using a given threshold value. Since the position of a treatment tool that holds a needle and a suture lies in the NEAR direction with respect to the position of tissue, the in-focus object plane position is preferentially moved in the NEAR direction in the needle-suture mode. In order to preferentially move the in-focus object plane position in the NEAR direction, the threshold value N used in the step S273 is set to be equal to or smaller than half of the number of effective blocks (e.g., equal to or smaller than 40% of the number of effective blocks). When the ratio of the number of NEAR blocks with respect to the total number of effective blocks is larger than the given threshold value, the in-focus direction is set to "NEAR" (S278). When the ratio of the number of NEAR blocks with respect to the total number of effective blocks is equal to or smaller than the given threshold value, the in-focus direction is set to "FAR" (S277).

The in-focus direction determination section 2080 outputs the in-focus direction determined as described above to the focus lens control section 2090. Note that the focus lens driving direction is "NEAR", "FAR", or "UNMOVING".

Figure 6:
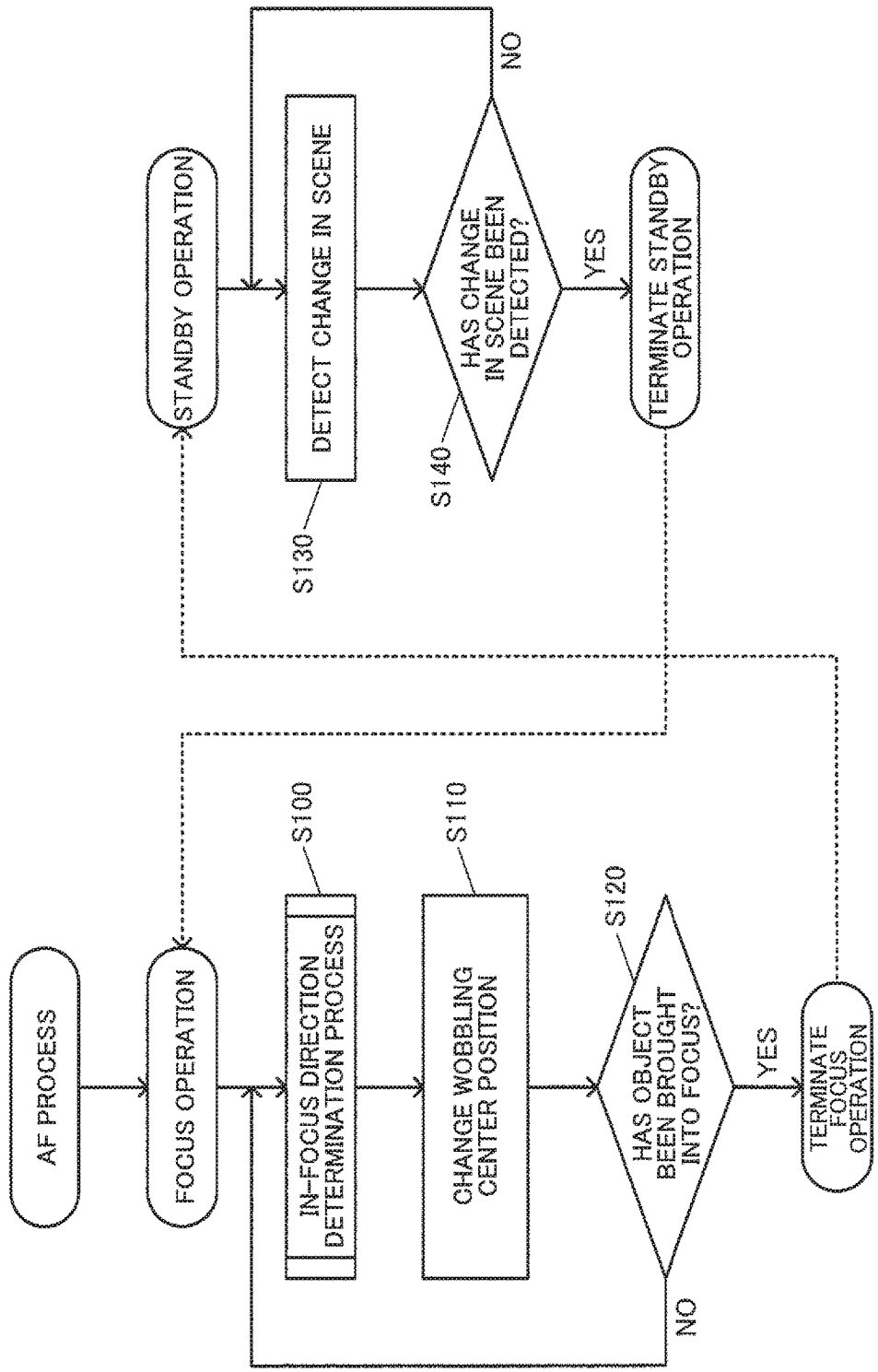
FIG. 6 is a flowchart illustrating a focus control process according to one embodiment of the invention.

The focus lens control section 2090 then changes the wobbling center position based on the determined in-focus direction (as described above in connection with the step S110 illustrated in FIG. 6).

4. Specific Example

FIGS. 13A to 14D illustrate an example of the object that is observed using an endoscope. The main object that is observed using an endoscope is tissue and a treatment tool (e.g., forceps). In FIGS. 13A and 14A, the dot-dash lines that extend from the end of the endoscope indicate the range that can be captured. FIGS. 13A and 14A are drawn on the assumption that the upper side corresponds to the left hand, the lower side corresponds to the right hand, the left side corresponds to the head, and the right side corresponds to the legs. Note that the positional relationship between the human body, the treatment tool, and the endoscope is not limited thereto. In FIGS. 13A and 14A, the in-focus object plane position refers to the in-focus position of the focus lens when the image was captured, and the target in-focus position refers to a position at which the object is brought into focus by means of the AF process.

FIG. 13A illustrates an example (scene) in which a treatment tool lies between the in-focus target object and the imaging device. In the example (scene) illustrated in FIG. 13A, the surface of tissue is determined to be the in-focus target object on the assumption that the user pays attention to tissue. FIG. 13B illustrates the in-focus direction determination result with respect to each evaluation block set to an image captured in a state in which the in-focus object plane position is the position A when the AF mode information that represents the tissue mode has been set to the mode setting section 2020, FIG. 13C illustrates the in-focus direction determination result with respect to each evaluation block set to an image captured in a state in which the in-focus object plane position is the position B when the AF mode information that represents the tissue mode has been set to the mode setting section 2020, and FIG. 13D illustrates the in-focus direction determination result with respect to each evaluation block set to an image captured in a state in which the in-focus object plane position is the position C when the AF mode information that represents the tissue mode has been set to the mode setting section 2020.

In FIG. 13B, since the in-focus direction determination result with respect to each evaluation block in which the treatment tool is captured is set to "NULL" by the null block setting section 2070, and most of the direction determination results with respect to the evaluation blocks are "FAR", the in-focus direction determination section 2080 outputs the direction "FAR". In FIG. 13C, the in-focus direction determination result with respect to each evaluation block in which the treatment tool is captured is set to "NULL" by the null block setting section 2070. However, the in-focus direction determination result with respect to an evaluation block in which tissue and the treatment tool are captured may be determined to be "NEAR", for example. Since the ratio of the number of evaluation blocks for which the direction determination result is determined to be "NEAR" to the total number of evaluation blocks is small, the ratio is smaller than the threshold value M set in the step S272, and the focus lens driving direction is set to "FAR" in the step S275. In FIG. 13D, since the in-focus direction determination result with respect to each evaluation block in which the treatment tool is captured is set to "NULL" by the null block setting section 2070, and most of the direction determination results are "NEAR", the focus lens driving direction is set to "NEAR".

When the AF process has been started from the in-focus object plane position A, the in-focus object plane position gradually approaches the target in-focus position as a result of repeating the steps S100 to S120. Even when the treatment tool is situated in the NEAR direction with respect to the in-focus object plane position, and tissue is situated in the FAR direction with respect to the in-focus object plane position (see the in-focus object plane position B), the in-focus object plane position gradually approaches the target in-focus position as a result of repeating the steps S100 to S120 without moving in an incorrect direction. When the AF process has been started from the in-focus object plane position C, the in-focus object plane position also gradually approaches the target in-focus position as a result of repeating the steps S100 to S120.

FIG. 14A illustrates an example (scene) in which tissue is situated at two positions that differ in the depth direction, and the surface of tissue that is situated closer to the endoscope occupies the majority of the imaging range (i.e., the user is paying attention to tissue that is situated closer to the endoscope). For example, FIG. 14A illustrates a scene in which membrane-like tissue E2 illustrated in FIG. 15A is pulled upward using forceps or the like (see FIG. 15B). Since tissue has a certain elasticity, tissue that differs from tissue that serves as a background is captured at a position closer to the endoscope in the same manner as in the example illustrated in FIG. 15B when tissue captured at the edge of the screen is moved toward the center of the image. When tissue is situated at two positions that differ in the depth direction, and the user is paying attention to the tissue that is situated on the rear side, it is considered that the position of the imaging section is adjusted so that the tissue that is situated on the front side does not lie within the imaging range, or does not occupy a large area within the AF evaluation area. For example, when the user is paying attention to tissue indicated by E1 illustrated in FIG. 15A, the state illustrated in FIG. 15B does not occur since it is unnecessary to moves the tissue indicated by E2 upward. Specifically, when tissue that is situated on the front side occupies a large area within the AF evaluation area data (see FIG. 15B, for example), it is considered that the target in-focus position is the surface of tissue that is situated close to the endoscope. FIG. 14B illustrates the in-focus direction determination result with respect to each evaluation block set to an image captured in a state in which the in-focus object plane position is the position A when the mode information that represents the tissue mode has been set to the mode setting section 2020, FIG. 14C illustrates the in-focus direction determination result with respect to each evaluation block set to an image captured in a state in which the in-focus object plane position is the position B when the mode information that represents the tissue mode has been set to the mode setting section 2020, and FIG. 14D illustrates the in-focus direction determination result with respect to each evaluation block set to an image captured in a state in which the in-focus object plane position is the position C when the mode information that represents the tissue mode has been set to the mode setting section 2020.

In FIG. 14B, since the in-focus direction determination result with respect to each evaluation block in which the treatment tool is captured is set to "NULL" by the null block setting section 2070, and most of the direction determination results are "FAR", the focus lens driving direction is set to "FAR". In FIG. 14C, since the in-focus direction determination result with respect to each evaluation block in which the treatment tool is captured is set to "NULL" by the null block setting section 2070, and the object that is situated in the NEAR direction with respect to the in-focus object plane position B occupies a large area within the AF evaluation area, the number of evaluation blocks determined to be "NEAR" increases. Therefore, the threshold value M set in the step S272 is exceeded, and the focus lens driving direction is set to "NEAR" in the step S272. In FIG. 14D, since the in-focus direction determination result with respect to each evaluation block in which the treatment tool is captured is set to "NULL" by the null block setting section 2070, and most of the direction determination results are "NEAR", the in-focus direction is set to "NEAR" in the step S272.

When the AF process has been started from the in-focus object plane position A, the in-focus object plane position gradually approaches the target in-focus position as a result of repeating the steps S100 to S120. When the AF process has been started from the in-focus object plane position B, the in-focus object plane position moves toward the target in-focus position without moving in an incorrect direction since the image information cannot be acquired from the tissue that is situated in the FAR direction and hidden behind the tissue that is situated in the NEAR direction. When the AF process has been started from the in-focus object plane position C, the in-focus object plane position also gradually approaches the target in-focus position as a result of repeating the steps S100 to S120.

Figure 16A:
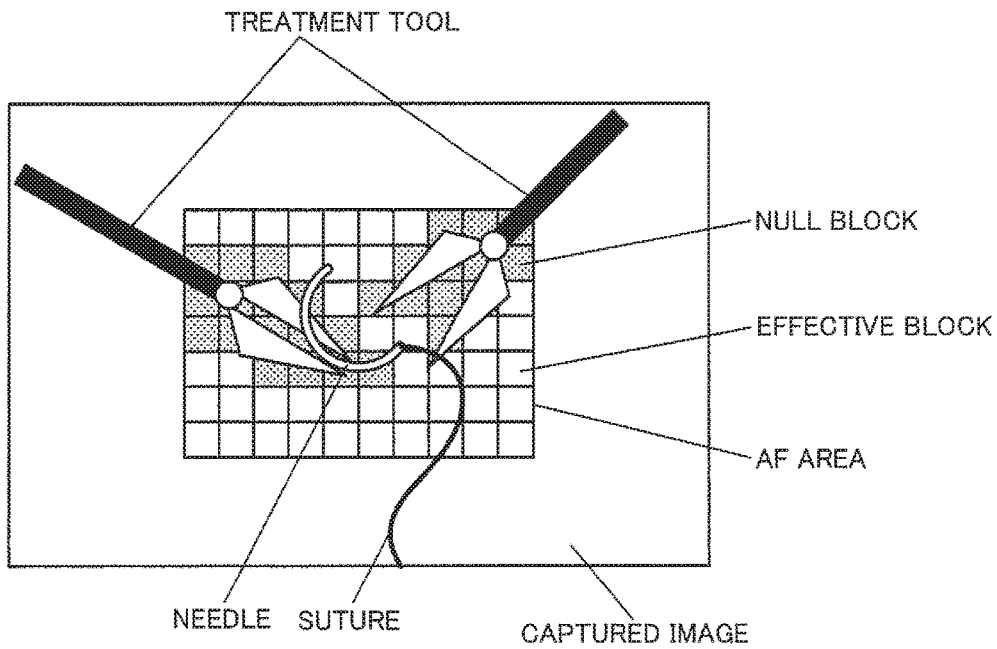
FIGS. 16A and 16B are views illustrating an effective block-null block setting example in each mode.
Figure 16B:
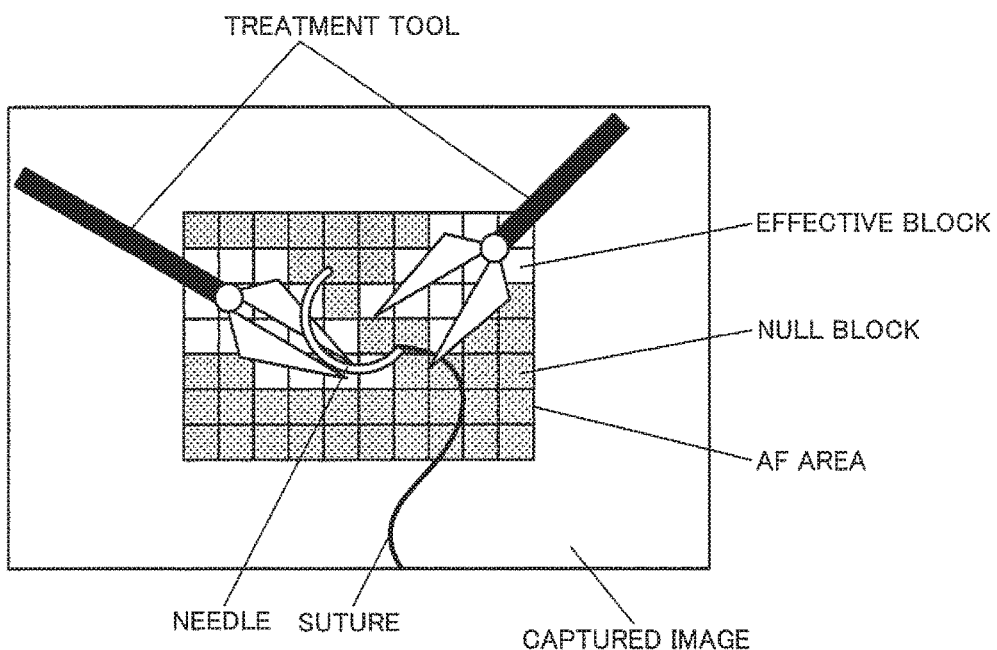

FIGS. 16A to 17D illustrate the difference between the tissue mode and the needle-suture mode. As illustrated in FIG. 16A, since tissue is the object of interest in the tissue mode, the blocks in which the treatment tool is captured are set to "NULL". As illustrated in FIG. 16B, since an area around the end of forceps that hold a needle and a suture is the object of interest in the needle-suture mode, the blocks in which tissue is captured are set to "NULL". FIG. 17B illustrates the in-focus direction determination result with respect to each block set to an image captured in a state in which the in-focus object plane position is the position A illustrated in FIG. 17A when the mode information that represents the needle-suture mode has been set to the mode setting section 2020, FIG. 14C illustrates the in-focus direction determination result with respect to each block set to an image captured in a state in which the in-focus object plane position is the position B illustrated in FIG. 17A when the mode information that represents the needle-suture mode has been set to the mode setting section 2020, and FIG. 14D illustrates the in-focus direction determination result with respect to each block set to an image captured in a state in which the in-focus object plane position is the position C illustrated in FIG. 17A when the mode information that represents the needle-suture mode has been set to the mode setting section 2020.

In FIG. 17B, since the in-focus direction determination result with respect to each evaluation block in which tissue is captured is set to "NULL" by the null block setting section 2070, and most of the direction determination results with respect to the effective blocks are "FAR", the ratio is determined to be smaller than the threshold value N in the step S273, and the in-focus direction is set to "FAR" in the step S278. In FIG. 17C, the in-focus direction determination result with respect to each evaluation block in which tissue is captured is set to "NULL" by the null block setting section 2070, and the in-focus direction determination result with respect to an evaluation block in which tissue and forceps are captured may be determined to be "FAR", for example. However, since the ratio of the number of effective blocks for which the direction determination result is determined to be "NEAR" increases, the threshold value N is exceeded in the step S273, and the in-focus direction is set to "NEAR" in the step S278. In FIG. 17D, since the in-focus direction determination result with respect to each evaluation block in which tissue is captured is set to "NULL" by the null block setting section 2070, and most of the direction determination results with respect to the effective blocks are "NEAR", the ratio is determined to be smaller than the threshold value N in the step S273, and the in-focus direction is set to "NEAR" in the step S278.

When the AF process has been started from the in-focus object plane position A, the in-focus object plane position gradually approaches the target in-focus position as a result of repeating the steps S100 to S120. Even when the treatment tool is situated in the NEAR direction with respect to the in-focus object plane position, and tissue is situated in the FAR direction with respect to the in-focus object plane position (see the in-focus object plane position B), the in-focus object plane position gradually approaches the target in-focus position as a result of repeating the steps S100 to S120 without moving in an incorrect direction. When the AF process has been started from the in-focus object plane position C, the in-focus object plane position also gradually approaches the target in-focus position as a result of repeating the steps S100 to S120.

Figure 18:
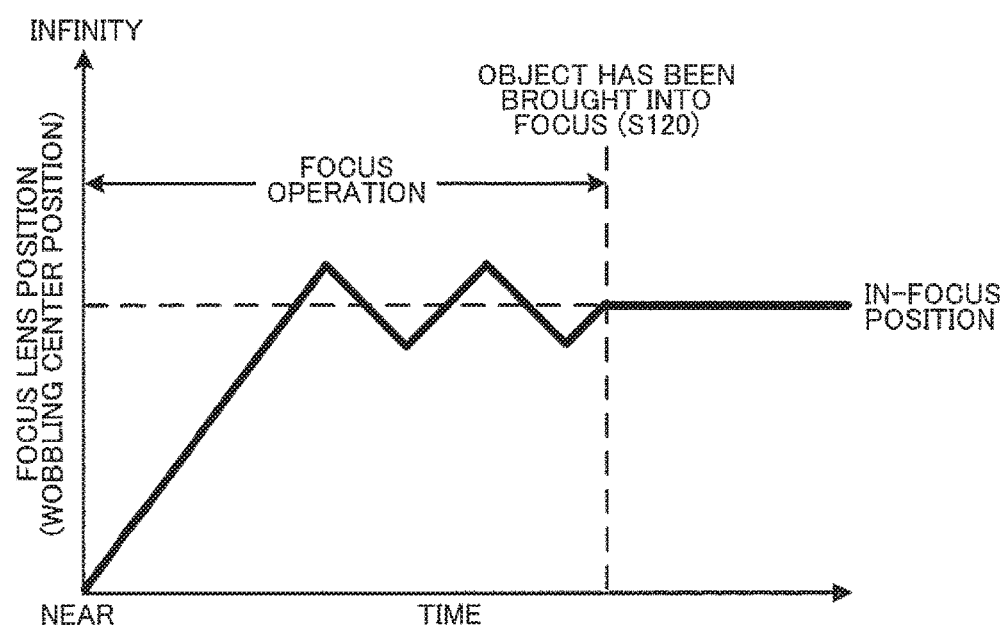
FIG. 18 is a view illustrating a time-series change in wobbling center position.

FIG. 18 illustrates an example of the movement of the wobbling center position until the in-focus object plane position coincides with the target in-focus position. In FIG. 18, the AF process is started from the position situated in the NEAR direction, and the in-focus object plane position approaches the target in-focus position as a result of repeating the steps S100 to S120. The in-focus object plane position may be situated in the FAR direction with respect to the target in-focus position. The in-focus direction is set to "NEAR" when the steps S100 to S120 are performed on an image captured at a timing at which the in-focus object plane position has been situated in the FAR direction with respect to the target in-focus position. As illustrated in FIG. 18, since the in-focus object plane position is moved around the target in-focus position after a given time has elapsed, the in-focus object plane position is situated very close to the target in-focus position at a timing at which it has been determined by the in-focus determination process (S120) that the object has been brought into focus.

According to the embodiments of the invention described above, an area that is of interest to the user of an endoscope (i.e., an area to which the user of an endoscope is paying attention) is estimated using the direction determination result with respect to each evaluation area, and the focus lens is driven based on the estimation results. This makes it possible to bring the object of interest into focus without requiring the user to perform a complex operation. When the AF mode has been set to the needle-suture mode, an area that is of interest to the user is estimated in a different way, as described above. This makes it possible to bring the object of interest into focus while preventing a situation in which tissue is necessarily brought into focus.

The focus control section 2095 may calculate at least one of area information about an area for which it has been determined that the target in-focus position lies in the NEAR direction, and area information about an area for which it has been determined that the target in-focus position lies in the FAR direction, based on the direction determination result, and may determine whether to perform the focus control process that moves the in-focus object plane position in the NEAR direction, or the focus control process that moves the in-focus object plane position in the FAR direction, based on whether or not the area information satisfies a given condition.

It suffices that the area information be information that represents an area. The area information is not limited to an area itself. For example, when each area (each evaluation block) has an identical size (see FIGS. 8A and 8B), the area is information that is proportional to the number of evaluation blocks. Therefore, the number of evaluation blocks for which it has been determined that the target in-focus position lies in the NEAR direction, or the number of evaluation blocks for which it has been determined that the target in-focus position lies in the FAR direction, may be used as the area information. The area information may represent a relative value. For example, the area information may represent a ratio with respect to the area of a given area. More specifically, the ratio of the area or the number of evaluation blocks for which it has been determined that the target in-focus position lies in the NEAR direction, to the area or the number of effective blocks (i.e., evaluation blocks other than null blocks) (see above) may be used as the area information. The above ratio need not necessarily be calculated with respect to the effective blocks. The ratio with respect to the AF area or the entire captured image may be used as the area information, for example. Note that it is desirable to change the determination reference (e.g., threshold value) that is used for the moving direction determination process when the area that is used to calculate the ratio is changed.

This makes it possible to determine the moving direction of the in-focus object plane position (in-focus direction) using the area information. Although an example in which the ratio of evaluation blocks for which it has been determined that the target in-focus position lies in the NEAR direction is calculated as the area information (see the steps S272 and S273 illustrated in FIG. 12), has been described above, the area information about evaluation blocks for which it has been determined that the target in-focus position lies in the FAR direction may also be used. The embodiments have been described above on the assumption that the imaging section 200 is operated so that the desired object can be captured so as to be easily observed. Specifically, it is likely that the object of interest occupies a large area within the captured image, and it is possible to appropriately determine the object of interest by utilizing the area information, and bring the object into focus. However, since an object that is situated away from the imaging section 200 is preferentially brought into focus in the tissue mode, priority with respect to the movement in the NEAR direction decreases in the tissue mode. Specifically, a condition whereby the in-focus object plane position is moved in the NEAR direction is less easily satisfied as compared with a condition whereby the in-focus object plane position is moved in the FAR direction when these conditions are used as the given condition.

The focus control section 2095 may perform the focus control process that moves the in-focus object plane position in the FAR direction when a value represented by the area information about an area for which it has been determined that the target in-focus position lies in the NEAR direction is equal to or smaller than a given NEAR area threshold value, or a value represented by the area information about an area for which it has been determined that the target in-focus position lies in the FAR direction is equal to or larger than a given FAR area threshold value, and moves the in-focus object plane position in the NEAR direction when the value represented by the area information about an area for which it has been determined that the target in-focus position lies in the NEAR direction is larger than the NEAR area threshold value, or the value represented by the area information about an area for which it has been determined that the target in-focus position lies in the FAR direction is smaller than the FAR area threshold value.

The NEAR area threshold value that is compared with the area information about an area for which it has been determined that the target in-focus position lies in the NEAR direction is the threshold value M (see the step S272) or the threshold value N (see the step S273) illustrated in FIG. 12.

A case where the area information about an area for which it has been determined that the target in-focus position lies in the FAR direction is compared with the FAR area threshold value has not been described above. When each area information represents the ratio with respect to the effective blocks, the sum of the value represented by the area information about an area for which it has been determined that the target in-focus position lies in the NEAR direction, and the value represented by the area information about an area for which it has been determined that the target in-focus position lies in the FAR direction, is 100(%). Specifically, when "FAR area threshold value=100-NEAR area threshold value (%)", a condition whereby the area information about an area for which it has been determined that the target in-focus position lies in the NEAR direction is equal to or smaller than the NEAR area threshold value is synonymous with a condition whereby the area information about an area for which it has been determined that the target in-focus position lies in the FAR direction is equal to or larger than the FAR area threshold value, and it is of no considerable significance to determine whether or not both these conditions are satisfied. Note that the threshold value may be set and the determination method may be modified in various ways in the same manner as the area information.

The above configuration makes it possible to determine the in-focus direction by means of the threshold value determination process. In this case, it is possible to implement a flexible determination process by appropriately changing the threshold value. For example, when the NEAR determination threshold value (=M) used in the tissue mode is increased, the in-focus object plane position is moved in the FAR direction unless an area for which it has been determined that the target in-focus position lies in the NEAR direction is sufficiently large. Therefore, it is possible to preferentially brings an object that is situated away from the imaging section 200 into focus. The threshold value M is larger than 50 (50 to 70 in a narrow sense), for example. In this case, the in-focus direction is the FAR direction unless an area for which it has been determined that the target in-focus position lies in the NEAR direction occupies more than half of the captured image. When the AF mode has been set to an exception mode (needle-suture mode) with respect to the principle that an object that is situated away from the imaging section 200 is brought into focus, it is possible to preferentially bring an object that is situated close to the imaging section 200 into focus by utilizing the threshold value N that is smaller than the threshold value M as the NEAR area threshold value.

The focus control section 2095 may perform a correction process that corrects the direction determination result with respect to a given area based on a time-series change in the direction determination result with respect to the given area, and may determine whether to perform the focus control process that moves the in-focus object plane position in the NEAR direction, or the focus control process that moves the in-focus object plane position in the FAR direction, based on the direction determination result subjected to the correction process.

An example in which the direction determination result with respect to each evaluation block is not changed has been described above using the flowcharts. Note that the correction process may be performed on the direction determination result, and the direction determination result that has been calculated may be changed. As described above with reference to FIG. 9 in connection with the reliability, it is normally likely that the same direction determination result is consecutively obtained with respect to a given block. For example, when the in-focus object plane position A is used as the wobbling center position in FIG. 13A, the in-focus direction is determined to be the FAR direction for a while with respect to the effective block (i.e., a block in which tissue is captured). Specifically, it is difficult to accurately adjust the in-focus object plane position if the wobbling center position suddenly changes from the position A to the position C, and it is considered that the wobbling center position gradually changes from the position A to the position C.

When the direction determination result with respect to a block in which a treatment tool is captured is used in the tissue mode (e.g., when a null block is not set, or when a null block is set, and tissue and a treatment tool are captured within one block), the direction determination result changes in the vicinity of the position D at which the in-focus object plane position corresponds to the position of the treatment tool. However, it is considered that the direction determination result becomes stable if the direction determination results obtained at positions on either side of the position D are taken into consideration.

The wobbling center position changes as illustrated in FIG. 18 in the vicinity of the correct-answer in-focus position, and the direction determination result with respect to an evaluation block in which the target object is captured changes frequently. However, it is considered that the direction determination result does not change frequently in a situation other than such an exceptional situation.

An example in which a time-series change in the direction determination result may be used to calculate the reliability has been described above in view of the above point. Note that the process is not limited thereto. For example, the direction determination result may be corrected using a time-series change in the direction determination result. For example, when the direction determination result has suddenly changed to "FAR" in a state in which the direction determination result "NEAR" has been successively obtained, the direction determination result may be corrected to "NEAR" on the assumption that the direction determination result "FAR" is an error. When it is unnecessary to perform a real-time process, it is possible to acquire the direction determination result with respect to a frame that follows the processing target frame in terms of time. In this case, it is possible to detect a situation in which the direction determination result has changed to "FAR" in a state in which the direction determination result "NEAR" has been successively obtained, and the direction determination result "NEAR" has been successively obtained thereafter, for example. In such a case, it is highly likely that the direction determination result "FAR" is an error, and the direction determination result with respect to the frame for which the direction determination result "FAR" has been obtained may be corrected to "NEAR".

The focus control section 2095 may have a first mode in which an area among the plurality of areas that is situated away from the imaging section 200 is preferentially brought into focus, and a second mode in which an area among the plurality of areas that is situated close to the imaging section 200 is preferentially brought into focus.

The first mode is the tissue mode in a narrow sense, and the second mode is the needle-suture mode (treatment tool mode) in a narrow sense. This makes it possible to flexibly change the focus control process instead of merely preferentially bringing an area that is situated away from the imaging section 200 into focus. An area that is situated away from the imaging section 200 is preferentially brought into focus since it is considered that tissue (object of interest) is captured within an area that is situated away from the imaging section 200 when the image is an in vivo image (see above). Specifically, when tissue is not the object of interest, the object of interest may not be brought into focus as a result of preferentially bringing an area that is situated away from the imaging section 200 into focus. It is possible to deal with various situations by switching the focus control process depending on the mode.

The focus control section 2095 may switch the mode between the first mode and the second mode based on an operation performed by the user.

This makes it possible to switch the mode based on an operation performed by the user. Note that the user performs an operation using an operation section, for example. The operation section may be provided to the imaging section 200, or may be implemented by the external I/F section 500. The mode may be switched using another method. For example, the mode may be automatically switched by the focus control device.

The focus control section 2095 may perform the focus control process in the first mode using a first condition as the given condition, and may perform the focus control process in the second mode using a second condition that differs from the first condition as the given condition.

The given condition is a condition that uses the area information. The given condition is a condition whereby whether to perform the focus control process that moves the in-focus object plane position in the NEAR direction, or the focus control process that moves the in-focus object plane position in the FAR direction, is determined.

This makes it possible to change the condition used when moving the in-focus object plane position corresponding to the mode. In other words, either an area that is situated away from the imaging section 200, or an area that is situated close to the imaging section 200, can be preferentially brought into focus by changing the condition corresponding to the mode. For example, when a condition whereby the value represented by the area information satisfies a given relationship with respect to the threshold value is used (see above), the condition is changed by changing the threshold value. When the area information about the NEAR block is compared with the NEAR area threshold value, the threshold value M is used as the NEAR area threshold value in the first mode (tissue mode), and the threshold value N (<M) is used as the NEAR area threshold value in the second mode (needle-suture mode) (see the steps S272 and S273 illustrated in FIG. 12). The NEAR area threshold value is set so that it is possible to determine whether or not an area for which it has been determined that the target in-focus position lies in the NEAR direction is predominant (see above). For example, the threshold value M is a value that corresponds to an area that is larger than 50% of the total area of the effective blocks (i.e., evaluation blocks other than null blocks).

The focus control section 2095 may calculate the feature quantity with respect to each of the plurality of areas, and may set a null area based on the feature quantity, the null area being an area for which the direction in which the in-focus object plane position is moved is not determined.

This makes it possible to implement a process that uses the feature quantity with respect to each area. More specifically, the object captured within each area may be determined from the feature quantity. In this case, it is possible to determine whether or not the object of interest is captured within each area by utilizing the feature quantity. It is possible to prevent a situation in which an inappropriate area is brought into focus by setting an area in which the object of interest is not captured to be the null area (null block) that is not subjected to the subsequent process.

Specifically, the focus control section 2095 may set an area among the plurality of areas for which it has been determined that an object other than tissue is captured, to be the null area based on the feature quantity. More specifically, the focus control section 2095 may set an area for which it has been determined that an object other than tissue is captured, to be the null area in the first mode, and may set an area for which it has been determined that tissue is captured, to be the null area in the second mode.

This makes it possible to set an appropriate area to be the null area corresponding to the mode. Specifically, it is possible to prevent a situation in which an object other than tissue is brought into focus in the tissue mode by setting an object other than tissue to be the null area, and prevent a situation in which tissue is brought into focus in a mode (needle-suture mode in a narrow sense) other than the tissue mode by setting tissue to be the null area.

Although an example in which the null area is used has been described above, an effective area may be set, and the process that determines the direction in which the in-focus object plane position is moved may be performed on the effective area. More specifically, the focus control section 2095 may calculate the feature quantity with respect to each of the plurality of areas, and may set an effective area based on the feature quantity, the effective area being an area among the plurality of areas for which the direction in which the in-focus object plane position is moved is determined.

This also makes it possible to prevent a situation in which an inappropriate area is brought into focus since an area in which the object of interest is captured is selected, and subjected to the subsequent process.

Specifically, the focus control section 2095 may set an area among the plurality of areas for which it has been determined that tissue is captured, to be the effective area based on the feature quantity. More specifically, the focus control section 2095 may set an area for which it has been determined that tissue is captured, to be the effective area in the first mode, and may set an area for which it has been determined that an object other than tissue is captured, to be the effective area in the second mode.

The weight (degree of contribution) of each area with respect to the process that determines the direction in which the in-focus object plane position is moved need not necessarily be limited to 1 or 0. An intermediate value may be set as the weight. A weight of 1 corresponds to the effective area or an area other than the null area, and a weight of 0 corresponds to the null area or an area other than the effective area. Specifically, the focus control section 2095 may calculate the feature quantity with respect to each of the plurality of areas, and may set weight information based on the feature quantity, the weight information representing the weight of each of the plurality of areas used when determining the direction in which the in-focus object plane position is moved.

In this case, the focus control section 2095 may increase the weight of an area for which it has been determined that tissue is captured (for which it has been determined that it is likely that tissue is captured), in the first mode, and may increase the weight of an area for which it has been determined that an object other than tissue is captured (for which it has been determined that it is likely that an object other than tissue is captured), in the second mode. More specifically, a feature quantity that corresponds to tissue may be set in advance, and the correlation between the feature quantity calculated from each area and the feature quantity that corresponds to tissue may be used. Since it is likely that tissue is captured when the correlation is high, the weight is increased in the first mode, and decreased in the second mode. Likewise, a feature quantity that corresponds to an object other than tissue may be set in advance, and the correlation between the feature quantity calculated from each area and the feature quantity that corresponds to an object other than tissue may be used. Since it is likely that an object other than tissue is captured when the correlation is high, the weight is decreased in the first mode, and increased in the second mode. The degree of correlation may be calculated in various ways. For example, the Mahalanobis distance between the feature quantities may be calculated, and it may be determined that the correlation is high when the Mahalanobis distance is short.

When the weight information is set, the area information is weighted using the weight information instead of directly using the area information when determining the direction in which the in-focus object plane position is moved. For example, a value "area information×weight information" may be calculated with respect to each evaluation block, and the sum of the values "area information×weight information" with respect to the evaluation blocks for which it has been determined that the target in-focus position lies in the NEAR direction may be used as the area information about the NEAR blocks. This also applies to the case where the area information about the FAR blocks is used.

The direction determination section 2040 may calculate the reliability that represents the probability that the direction determination result with respect to each area is reliable.

This makes it possible to determine whether or not the direction determination result is reliable. In this case, the focus control section 2095 may set a null area based on the reliability, the null area being an area for which the direction in which the in-focus object plane position is moved is not determined (see FIG. 10, for example). According to this configuration, when the direction determination result with respect to a given area is not reliable, the given area can be excluded from the processing target, and it is possible to prevent a situation in which an inappropriate direction is determined to be the in-focus direction.

The area setting section 2010 may change at least one of the positions, the size, and the number of the areas to be set to the captured image when the focus control section 2095 has set the mode to the second mode as compared with a case where the focus control section 2095 has set the mode to the first mode.

This makes it possible to set an appropriate area to be the null area corresponding to the mode (i.e., corresponding to the object of interest in each mode in a narrow sense). In the second mode illustrated in FIG. 8B, the size of the areas (evaluation blocks) is small, and the number of areas (evaluation blocks) is large as compared with the first mode illustrated in FIG. 8A. This is because the object of interest (i.e., needle and suture) in the second mode is small and thin as compared with the object of interest (i.e., tissue) in the first mode. The AF area may be set to a lower part of the image in the second mode as compared with the first mode (see above). In this case, the positions of the evaluation blocks also change.

The direction determination section 2040 may perform the direction determination process using a position based on the in-focus object plane position at a timing at which the captured image that is subjected to the direction determination process has been acquired, as the reference position.

Specifically, the embodiments implement the focus control process that utilizes wobbling. In this case, it suffices that the direction in which the in-focus object plane position is moved with respect to the current position be determined at each processing timing. In this case, the in-focus object plane position that corresponds to the processing target timing, or a position determined from the in-focus object plane position that corresponds to the processing target timing, may be used as the reference position. More specifically, the in-focus object plane position that corresponds to the wobbling center position may be used as the reference position.

The direction determination section 2040 may calculate the AF evaluation value with respect to each area from a plurality of captured images that include a first captured image and a second captured image, and may perform the direction determination process based on a comparison process performed on the AF evaluation value calculated from the first captured image and the AF evaluation value calculated from the second captured image, the first captured image being an image captured in a state in which the in-focus object plane position lies in the NEAR direction with respect to the reference position, and the second captured image being an image captured in a state in which the in-focus object plane position lies in the FAR direction with respect to the reference position.

This makes it possible to implement the focus control process that utilizes wobbling. Specifically, the direction in which the in-focus object plane position is moved with respect to the current position is determined at each processing timing. More specifically, an image captured when the in-focus object plane position is moved in the NEAR direction with respect to the current position (reference position), is compared with an image captured when the in-focus object plane position is moved in the FAR direction with respect to the current position (reference position). The AF evaluation value such as a contrast value may be used for the comparison process.

The focus control device according to the embodiments of the invention can be interpreted from a different viewpoint (aspect). Specifically, the focus control device according to the embodiments of the invention may include an image acquisition section (e.g., an interface (e.g., A/D conversion section 310 (see FIG. 3)) with the imaging section 200 in a narrow sense) that acquires a captured image that has been captured by the imaging section 200, and the focus control section 2095 that performs the focus control process that utilizes wobbling. When the in-focus object plane position that corresponds to a wobbling reference position lies between tissue and a treatment tool, the focus control section 2095 performs the focus control process that utilizes wobbling that preferentially moves the in-focus object plane position in a first direction as compared with a second direction, the first direction being a direction toward the tissue with respect to the in-focus object plane position that corresponds to the wobbling reference position, and the second direction being a direction toward the treatment tool with respect to the in-focus object plane position that corresponds to the wobbling reference position.

When the image is an image in which tissue is captured (in vivo image in a narrow sense), it is likely that the user pays attention to tissue, and a treatment tool or the like serves as an obstacle during the focus control process (see above). Therefore, the direction in which the in-focus object plane position is moved by wobbling (i.e., the direction in which the in-focus object plane position that corresponds to the wobbling center position is moved) may be set so that the in-focus object plane position is easily moved toward tissue.

The above process may be implemented in various ways. For example, the focus control section 2095 may determine whether or not the object captured within the captured image is tissue based on the feature quantity calculated from the captured image, and may perform the focus control process that utilizes wobbling using the direction in which the object determined to be tissue is brought into focus as the first direction.

In this case, since it is possible to determine whether the object captured within each area is tissue or an object other than tissue in the same manner as in the case where the above null block setting method is used, it is possible to preferentially move the in-focus object plane position in the first direction by performing the focus control process on an area for which it has been determined that tissue is captured.

Alternatively, it is possible to perform the focus control process while giving priority to an area for which it is likely that tissue is captured without directly determining whether or not the object is tissue. For example, the focus control section 2095 may determine that an area that has been determined to have a large area within the captured image is an area that corresponds to tissue based on the area information about each area of the captured image, and may perform the focus control process that utilizes wobbling using the direction in which the area that has been determined to correspond to tissue is brought into focus as the first direction.

In this case, since information such as color is not used, it is impossible to directly determine whether or not the object captured within each area is tissue. However, it is likely that the user is paying attention to tissue, and the object to which the user is paying attention occupies a large area within the captured image in a situation to which the embodiments of the invention are applied. Specifically, it is possible to determine an area that is estimated to be tissue by utilizing the area information about the image. In other words, it is possible to implement the focus control process that preferentially beings tissue into focus by performing the focus control process based on the area information.

The embodiments of the invention are not limited to the focus control device, and may also be applied to an endoscope apparatus (endoscope system) that includes the focus control device. Specifically, the embodiments of the invention may be applied to the endoscope system illustrated in FIG. 3. In this case, the captured image is an in vivo image, and it is possible to implement an endoscope apparatus that can preferentially bring tissue that is situated away from the imaging section 200 into focus, and can optionally bring tissue that is situated on the front side, a treatment tool, or the like into focus.

The focus control device and the like according to the embodiments of the invention may include a processor and a memory. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an application-specific integrated circuit (ASIC). The memory stores a computer-readable instruction. Each section of the focus control device and the like according to the embodiments of the invention is implemented by causing the processor to execute the instruction. The memory may be a semiconductor memory (e.g., SRAM or DRAM), a register, a hard disk, or the like. The instruction may be an instruction included in an instruction set that is included in a program, or may be an instruction that causes a hardware circuit included in the processor to operate.

Although only some embodiments of the present invention have been described in detail above, those skilled in the art will readily appreciate that many modifications are possible in the embodiments without materially departing from the novel teachings and advantages of the invention. Accordingly, all such modifications are intended to be included within scope of this invention. Any term cited with a different term having a broader meaning or the same meaning at least once in the specification and the drawings can be replaced by the different term in any place in the specification and the drawings. The configurations and the operations of the focus control device and the endoscope apparatus are not limited to those described above in connection with the embodiments. Various modifications and variations may be made of those described above in connection with the embodiments.

What is claimed is:

1. An endoscope focus control device comprising:
a processor comprising hardware, the processor being configured to implement:
an area setting process that sets a plurality of areas to a captured image that has been captured by an imaging section, each of the plurality of areas including a plurality of pixels;
a direction determination process that determines whether a target in-focus position lies in a NEAR direction or a FAR direction with respect to a reference position with respect to at least two of the plurality of areas set to the captured image to calculate a direction determination result with respect to each of the plurality of areas, the target in-focus position being a target of an in-focus object plane position, and the direction determination result indicating one of NEAR, FAR, and NULL; and
a focus control process that preferentially brings an area among the plurality of areas that is situated away from the imaging section into focus based on the direction determination result,
wherein the processor calculates at least one of area information about an area for which it has been determined that the target in-focus position lies in the NEAR direction, and the area information about an area for which it has been determined that the target in-focus position lies in the FAR direction, based on the direction determination result, and determines whether to perform the focus control process that moves the in-focus object plane position in the NEAR direction, or the focus control process that moves the in-focus object plane position in the FAR direction, based on whether or not the area information satisfies a given condition,
wherein the processor implements the focus control process that calculates a feature quantity with respect to each of the plurality of areas, and sets a null area based on the feature quantity, the null area being an area for which a direction in which the in-focus object plane position is moved is not determined, and
wherein the processor implements the focus control process that sets an area among the plurality of areas for which it has been determined that an object other than tissue is captured, to be the null area based on the feature quantity.

2. The endoscope focus control device as defined in claim 1, wherein the processor implements the focus control process that moves the in-focus object plane position in the FAR direction when a value represented by the area information about the area for which it has been determined that the target in-focus position lies in the NEAR direction is equal to or smaller than a given NEAR area threshold value, or a value represented by the area information about the area for which it has been determined that the target in-focus position lies in the FAR direction is equal to or larger than a given FAR area threshold value, and moves the in-focus object plane position in the NEAR direction when the value represented by the area information about the area for which it has been determined that the target in-focus position lies in the NEAR direction is larger than the NEAR area threshold value, or the value represented by the area information about the area for which it has been determined that the target in-focus position lies in the FAR direction is smaller than the FAR area threshold value.

3. The endoscope focus control device as defined in claim 1, wherein the processor implements a correction process that corrects the direction determination result with respect to a given area based on a time-series change in the direction determination result with respect to the given area, and determines whether to perform the focus control process that moves the in-focus object plane position in the NEAR direction, or the focus control process that moves the in-focus object plane position in the FAR direction, based on the direction determination result subjected to the correction process.

4. The endoscope focus control device as defined in claim 1, wherein the processor implements the focus control process in one of a first mode in which an area among the plurality of areas that is situated away from the imaging section is preferentially brought into focus, and a second mode in which an area among the plurality of areas that is situated close to the imaging section is preferentially brought into focus.

5. The endoscope focus control device as defined in claim 4, wherein the processor implements the area setting process that changes at least one of positions, a size, and a number of the areas to be set to the captured image when the focus control process is implemented in the second mode as compared with a case where the focus control process is implemented in the first mode.

6. The endoscope focus control device as defined in claim 4, wherein a mode in which the processor implements the focus control process is switchable between the first mode and the second mode based on an operation performed by a user.

7. The endoscope focus control device as defined in claim 1, wherein the processor implements the focus control process in one of a first mode in which an area among the plurality of areas that is situated away from the imaging section is preferentially brought into focus, and a second mode in which an area among the plurality of areas that is situated close to the imaging section is preferentially brought into focus, and
wherein the processor implements the focus control process in the first mode using a first condition as the given condition, and implements the focus control process in the second mode using a second condition that differs from the first condition as the given condition.

8. The endoscope focus control device as defined in claim 1, wherein the processor implements the focus control process that sets weight information based on the feature quantity calculated with respect to each of the plurality of areas, the weight information representing a weight of each of the plurality of areas used when determining a direction in which the in-focus object plane position is moved.

9. The endoscope focus control device as defined in claim 1, wherein the processor implements the focus control process in one of a first mode in which an area among the plurality of areas that is situated away from the imaging section is preferentially brought into focus, and a second mode in which an area among the plurality of areas that is situated close to the imaging section is preferentially brought into focus, and
wherein the processor sets an area among the plurality of areas for which it has been determined that an object other than tissue is captured, to be the null area in the first mode, and sets an area among the plurality of areas for which it has been determined that the tissue is captured, to be the null area in the second mode.

10. The endoscope focus control device as defined in claim 1, wherein the processor implements the focus control process that sets an effective area based on the feature quantity calculated with respect to each of the plurality of areas, the effective area being an area among the plurality of areas for which a direction in which the in-focus object plane position is moved is determined.

11. The endoscope focus control device as defined in claim 10, wherein the processor implements the focus control process in one of a first mode in which an area among the plurality of areas that is situated away from the imaging section is preferentially brought into focus, and a second mode in which an area among the plurality of areas that is situated close to the imaging section is preferentially brought into focus, and
wherein the processor sets an area among the plurality of areas for which it has been determined that tissue is captured, to be the effective area in the first mode, and sets an area among the plurality of areas for which it has been determined that an object other than the tissue is captured, to be the effective area in the second mode.

12. The endoscope focus control device as defined in claim 1, wherein the processor implements the direction determination process that calculates a reliability that represents a probability that the direction determination result with respect to each of the plurality of areas is reliable.

13. The endoscope focus control device as defined in claim 12, wherein the processor implements the focus control process that sets the null area based on the reliability.

14. The endoscope focus control device as defined in claim 1, wherein the processor implements the direction determination process using a position based on the in-focus object plane position at a timing at which the captured image that is subjected to the direction determination process has been acquired, as the reference position.

15. The endoscope focus control device as defined in claim 1, wherein the processor calculates an AF evaluation value with respect to each of the plurality of areas from a plurality of the captured images that include a first captured image and a second captured image, and implements the direction determination process based on a comparison process performed on the AF evaluation value calculated from the first captured image and the AF evaluation value calculated from the second captured image, the first captured image being an image captured in a state in which the in-focus object plane position lies in the NEAR direction with respect to the reference position, and the second captured image being an image captured in a state in which the in-focus object plane position lies in the FAR direction with respect to the reference position.

16. An endoscope apparatus comprising the endoscope focus control device as defined in claim 1.

17. An endoscope focus control device comprising:
a processor comprising hardware, the processor being configured to implement:
an area setting process that sets a plurality of areas to a captured image that has been captured by an imaging section, each of the plurality of areas including a plurality of pixels;
a direction determination process that determines whether a target in-focus position lies in a NEAR direction or a FAR direction with respect to a reference position with respect to at least two of the plurality of areas set to the captured image to calculate a direction determination result with respect to each of the plurality of areas, the target in-focus position being a target of an in-focus object plane position, and the direction determination result indicating one of NEAR, FAR, and NULL; and
a focus control process that preferentially brings an area among the plurality of areas that is situated away from the imaging section into focus based on the direction determination result,
wherein the processor calculates at least one of area information about an area for which it has been determined that the target in-focus position lies in the NEAR direction, and the area information about an area for which it has been determined that the target in-focus position lies in the FAR direction, based on the direction determination result, and determines whether to perform the focus control process that moves the in-focus object plane position in the NEAR direction, or the focus control process that moves the in-focus object plane position in the FAR direction, based on whether or not the area information satisfies a given condition,
wherein the processor implements the focus control process that calculates a feature quantity with respect to each of the plurality of areas, and sets an effective area based on the feature quantity, the effective area being an area among the plurality of areas for which a direction in which the in-focus object plane position is moved is determined, and
wherein the processor implements the focus control process that sets an area among the plurality of areas for which it has been determined that tissue is captured, to be the effective area based on the feature quantity.

18. A method for controlling a focus control device, the method comprising:
setting a plurality of areas to a captured image that has been captured by an imaging section, each of the plurality of areas including a plurality of pixels;
performing a direction determination process that determines whether a target in-focus position lies in a NEAR direction or a FAR direction with respect to a reference position with respect to at least two of the plurality of areas set to the captured image to calculate a direction determination result with respect to each of the plurality of areas, the target in-focus position being a target of an in-focus object plane position, and the direction determination result indicating one of NEAR, FAR, and NULL;
performing a focus control process that preferentially brings an area among the plurality of areas that is situated away from the imaging section into focus based on the direction determination result; and
calculating at least one of area information about an area for which it has been determined that the target in-focus position lies in the NEAR direction, and the area information about an area for which it has been determined that the target in-focus position lies in the FAR direction, based on the direction determination result, and determining whether to perform the focus control process that moves the in-focus object plane position in the NEAR direction, or the focus control process that moves the in-focus object plane position in the FAR direction, based on whether or not the area information satisfies a given condition,
wherein the focus control process calculates a feature quantity with respect to each of the plurality of areas, and setting a null area based on the feature quantity, the null area being an area for which a direction in which the in-focus object plane position is moved is not determined, and
wherein the focus control process sets an area among the plurality of areas for which it has been determined that an object other than tissue is captured, to be the null area based on the feature quantity.

* * * * *